(12) United States Patent
Weissman et al.

(10) Patent No.: US 9,045,734 B2
(45) Date of Patent: Jun. 2, 2015

(54) ISOLATION AND CHARACTERIZATION OF PROGENITOR CELLS FROM MESOTHELIUM

(71) Applicant: The Board of Trustees of the Leland Stanford Junior University, Palo Alto, CA (US)

(72) Inventors: Irving L. Weissman, Stanford, CA (US); Yuval Rinkevich, Sha'arei Tikva (IL)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/953,514

(22) Filed: Jul. 29, 2013

(65) Prior Publication Data

US 2014/0037590 A1 Feb. 6, 2014

Related U.S. Application Data

(60) Provisional application No. 61/677,806, filed on Jul. 31, 2012.

(51) Int. Cl.
*C12N 5/071* (2010.01)
*C12N 5/0775* (2010.01)
*C12N 5/077* (2010.01)

(52) U.S. Cl.
CPC ............ *C12N 5/0662* (2013.01); *C12N 5/0656* (2013.01); *C12N 5/0661* (2013.01); *C12N 5/0668* (2013.01)

(58) Field of Classification Search
CPC .. C12N 5/0661; C12N 5/0662; C12N 5/0656; C12N 5/0668
See application file for complete search history.

(56) References Cited

U.S. PATENT DOCUMENTS

2011/0104735 A1* 5/2011 Buehrer et al. ................. 435/29

OTHER PUBLICATIONS

Onitsuka et al., Characterization and functional analyses of hepatic mesothelial cells in mouse liver development, 2010, Gastroenterology 138(4): 1525-1535.*
Venneri et al., Identification of proangiogenic TIE2-expressing monocytes (TEMs) in human peripheral blood and cancer, 2007, Blood 109(12): 5276-5285.*
Kina et al., The monoclonal antibody TER- 119 recognizes a molecule associated with glycophorin A and specifically marks the late stages of murine erythroid lineage, British Journal of Haematology 109(2): 280-287.*
Argani; et al. "Mesothelin is Overexpressed in the Vast Majority of Ductal Adenocarcinomas of the Pancreas Identification of a New Pancreatic Cancer Marker by Serial Analysis of Gene Expression (SAGE)", Clinical Cancer Research (Dec. 2001), 7(12):3862-3868.
"Article: Researchers' work from University of Naples focuses on stem cell research", Highbeam Research (Nov. 2010), 3 pgs.
Cai; et al. "A myocardial lineage derives from Tbx18 epicardial cells", Nature (Jul. 2008), 454(7200):104-108.
Carmona; et al. "Peritoneal repairing cells: a type of bone marrow derived progenitor cells involved in mesothelial regeneration", J Cell Mol Med (May 2011),15(5):1200-1209.
Chen; et al. "Fibrocytes, the fibroblast progenitor cells of hematopoietic lineage, enhance cutaneous wound healing in diabetic mice", AAPS-89th Annual Meeting Abstracts (2010) Abstract.
Chong; et al. "Adult cardiac-resident MSC-like stem cells with a proepicardial origin", Cell Stem Cell (Dec. 2011), 9 (6):527-540.
Foley-Comer; et al. "Evidence for incorporation of free-floating mesothelial cells as a mechanism of serosal healing", J Cell Sci (Apr. 2002), 115(Pt 7):1383-1389.
Hoganson; et al. "Preserved extracellular matrix components and retained biological activity in decellularized porcine mesothelium", Biomaterials (Sep. 2010), 31(27):6934-6940, abstract only.
Manner; et al. "Does the subepicardial mesenchyme contribute myocardioblasts to the myocardium of the chick embryo heart? A quail-chick chimera study tracing the fate of the epicardial primordium", Anat Rec (Jun. 1999), 255 (2):212-226.
McCulloh; et al. "Discrimination of two fibroblast progenitor populations in early explant cultures of hamster gingiva", Cell Tissue Res (1991), 264:87-94.
Mikawa; et al. "Pericardial mesoderm generates a population of coronary smooth muscle cells migrating into the heart along with ingrowth of the epicardial organ", Dev Biol (Mar. 1996), 174(2):221-232.
Quan; et al. "Culture and Analysis of Circulating Fibrocytes", Methods Mol Med (2007), 135:423-434.
Smart; et al. "De novo cardiomyocytes from within the activated adult heart after injury", Nature (Jun. 2011), 474 (7353):640-644.
Strutz; et al. "Identification and characterization of a fibroblast marker: FSP1", J Cell Biol (Jul. 1995), 130 (2):393-405.
Wessels; et al. "The epicardium and epicardially derived cells (EPDCs) as cardiac stem cells", Anat Rec A Discov Mol Cell Evol Biol (Jan. 2004), 276(1):43-57.
Yung; et al. "Peritoneal mesothelial cell culture and biology", Perit Dial Int (Mar-Apr. 2006), 26(2):162-173.
Zhou; et al., "Epicardial progenitors contribute to the cardiomyocyte lineage in the developing heart", Nature (Jul. 2008), 454(7200):109-13.

* cited by examiner

*Primary Examiner* — Robert Yamasaki
(74) *Attorney, Agent, or Firm* — Bozicevic, Field & Francis LLP; Pamela J. Sherwood

(57) ABSTRACT

Populations enriched for smooth muscle progenitors are obtained by selection on the basis of expression of specific cell surface markers.

**9 Claims, 15 Drawing Sheets
(14 of 15 Drawing Sheet(s) Filed in Color)**

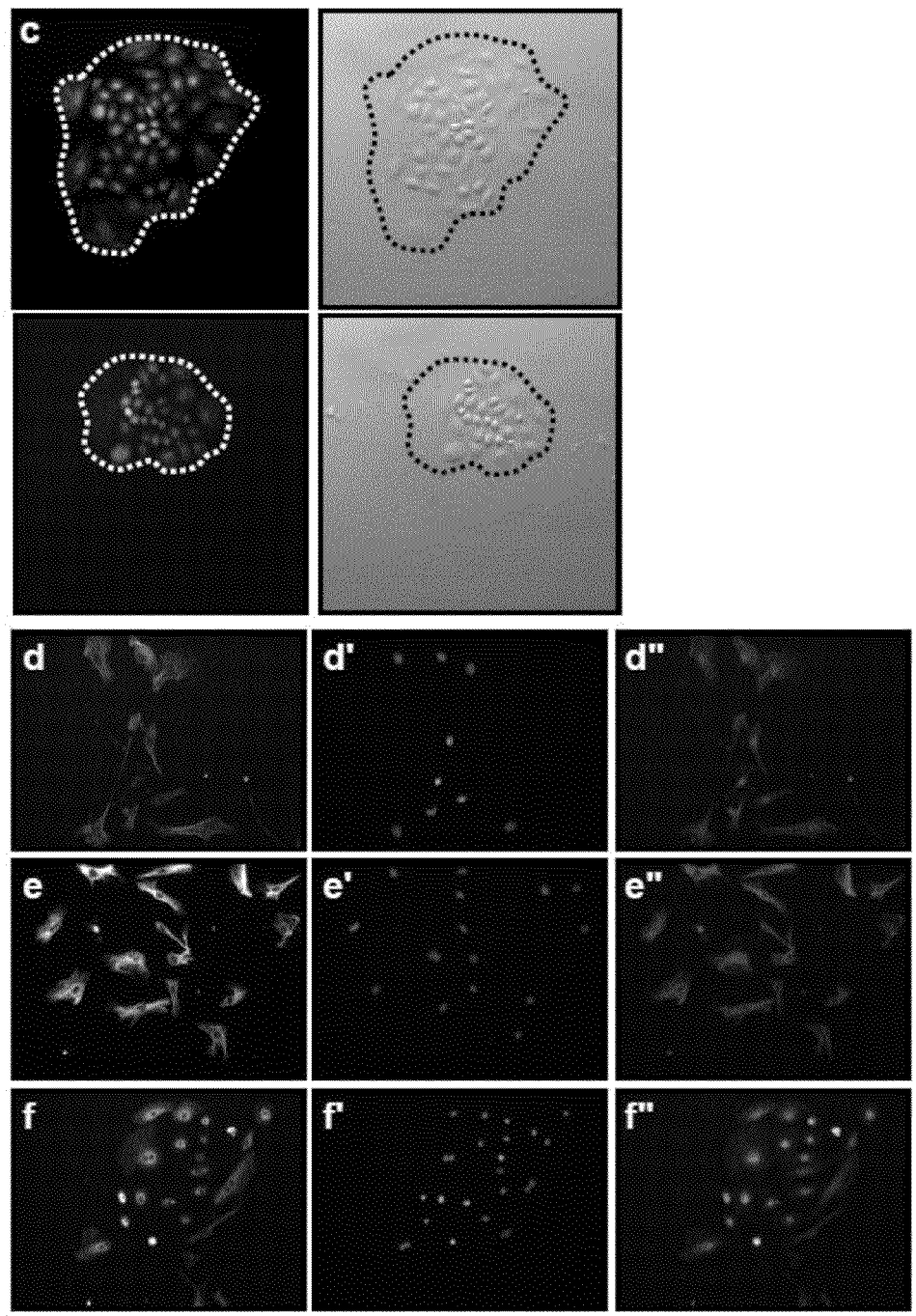

FIG. 3G-I
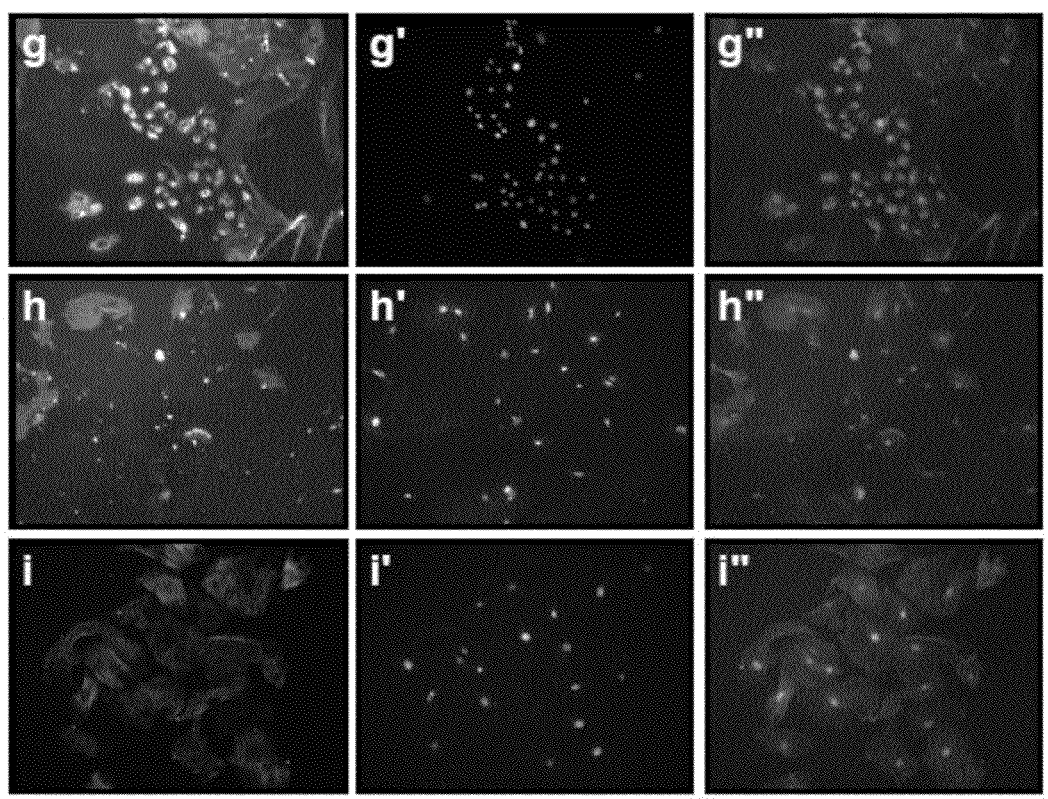

FIG. 4B-D
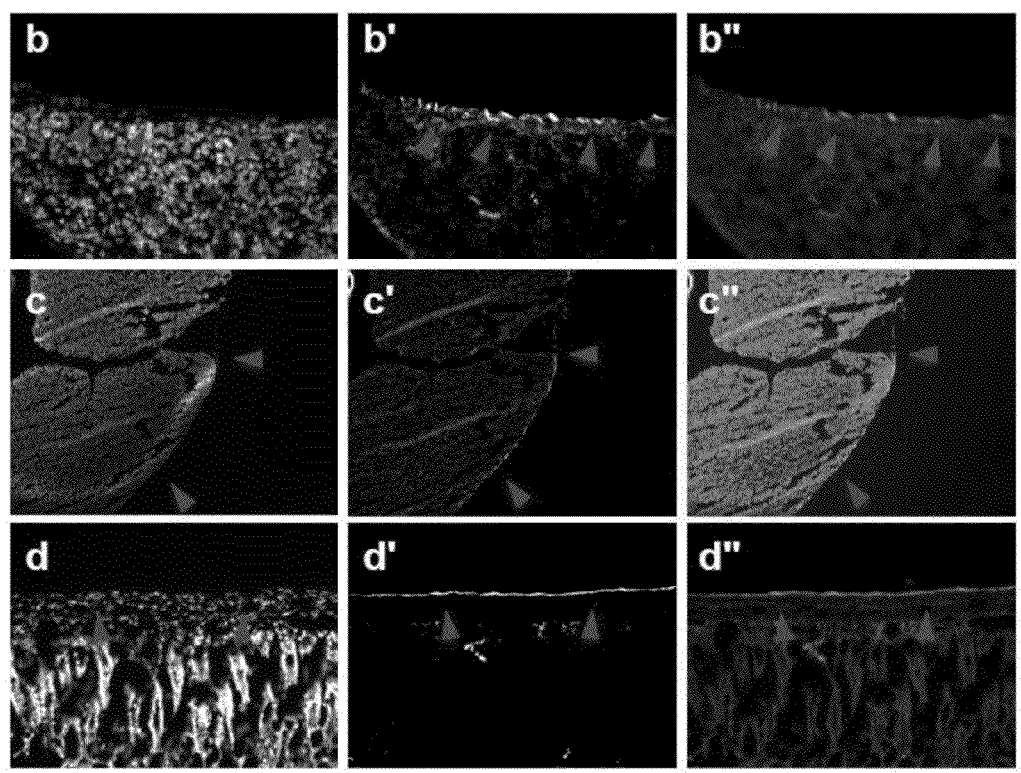

FIG. 4E-J
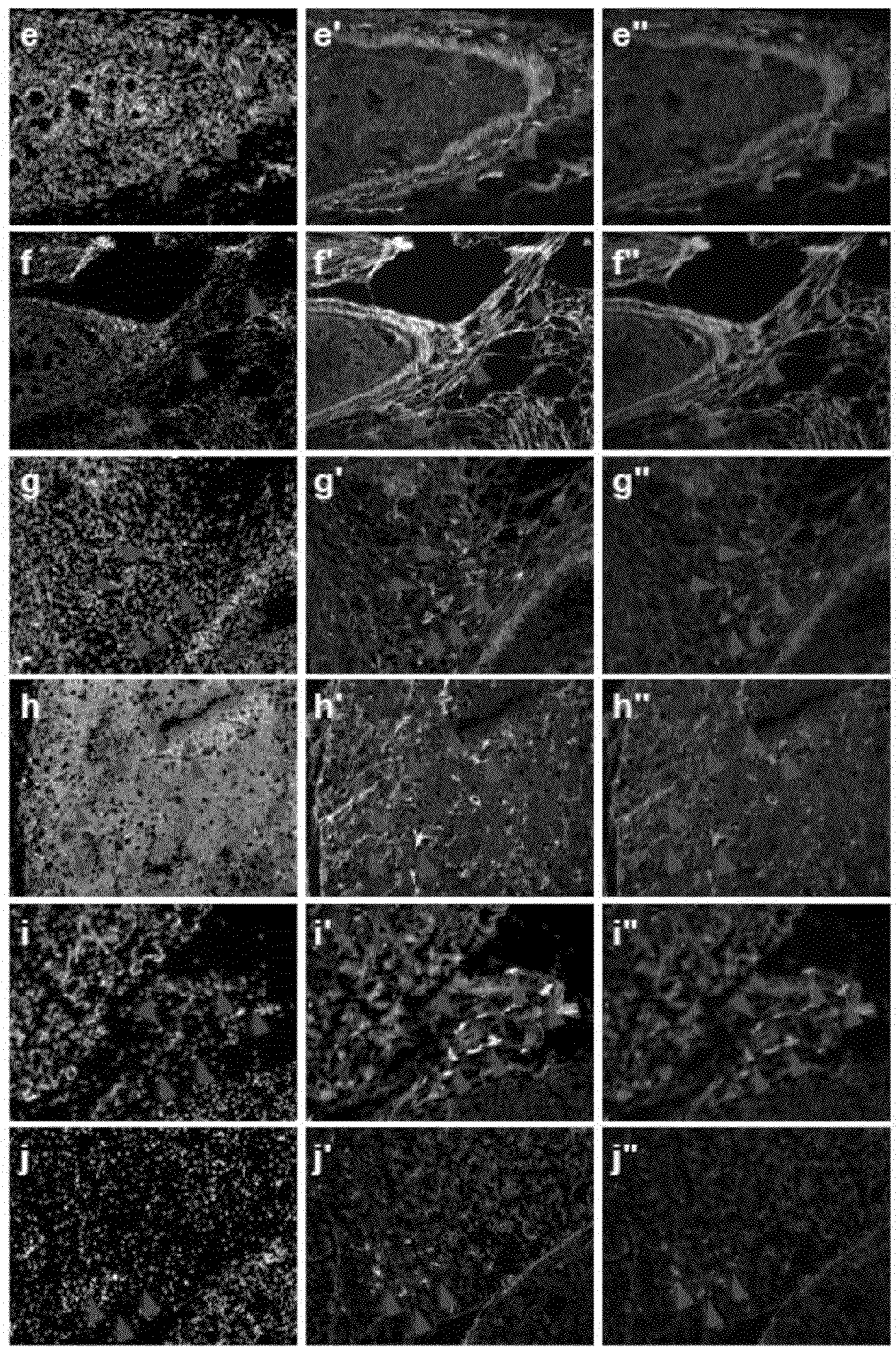

ISOLATION AND CHARACTERIZATION OF PROGENITOR CELLS FROM MESOTHELIUM

BACKGROUND OF THE INVENTION

Stem cells have a capacity both for self-renewal and the generation of differentiated cell types. This pluripotentiality makes stem cells unique. In addition to studying the important normal function of stem cells in the regeneration of tissues, researchers have further sought to exploit the potential of in situ and/or exogenous stem cells for the treatment of a variety of disorders. While early, embryonic stem cells have generated considerable interest, the stem cells resident in adult tissues may also provide an important source of regenerative capacity.

These somatic, or adult, stem cells are undifferentiated cells that reside in differentiated tissues, and have the properties of self-renewal and generation of differentiated cell types. The differentiated cell types may include all or some of the specialized cells in the tissue. For example, hematopoietic stem cells give rise to all hematopoietic lineages, but do not seem to give rise to stromal and other cells found in the bone marrow. Sources of somatic stem cells include bone marrow, blood, the cornea and the retina of the eye, brain, skeletal muscle, dental pulp, liver, skin, the lining of the gastrointestinal tract, and pancreas. Adult stem cells are usually quite sparse. Often they are difficult to identify, isolate, and purify. Often, somatic stem cells are quiescent until stimulated by the appropriate growth signals.

Progenitor or precursor cells are similar to stem cells, but are usually considered to be distinct by virtue of lacking the capacity for self-renewal. Researchers often distinguish precursor/progenitor cells from stem cells in the following way: when a stem cell divides, one of the two new cells is often a stem cell capable of replicating itself again. In contrast, when a progenitor/precursor cell divides, it forms two specialized cells, neither of which is capable of replicating itself. Progenitor/precursor cells can replace cells that are damaged or dead, thus maintaining the integrity and functions of a tissue such as liver or brain.

Fibroblasts and smooth muscle cells (FSMCs) undertake diverse cellular functions during embryonic development and in steady state adult tissues and organs. Morphologically, they are often defined as elongated, spindle-shaped cells that readily adhere to tissue culture substrates and migrate over these substrates. However, FSMCs may exhibit a variety of shapes and sizes, depending on the host tissue and its physiological and pathological state. During the development of the internal organs, and their vasculature, FSMCs are the predominant cell types within both stroma and the vasculature's tunica media and adventitia, that are believed to be involved in the synthesis and remodeling of the extra cellular matrix (ECM), becoming relatively quiescent in the steady-state adult tissues.

Within the vascular system, FSMCs maintain vascular tone and function by expressing and secreting contractile and elastic proteins within the tunica media and adventitia. However, chronic activity by FSMCs impedes organ function. As an outcome, FSMCs are the principal cell types that can accumulate in diverse medical conditions, including tissue and organ fibrosis, atherosclerosis, and formation of atheromatous plaque after blood vessel injury. FSMCs may also contribute to the progression of cancer by serving as key cellular components in the tumor stroma, a finding that could implicate the tumor-associated FSMC as an important target for anti-cancer therapy.

Based on these similarities in morphology and function, fibroblasts and smooth muscle cells have been proposed to arise from a common lineage. Central to our understanding of fibroblasts and smooth muscle cells is the question of their origin. Several ideas have been proposed as serving a source of FSMCs for the adult thoracic and abdominal [coelomic] cavities and internal organs. The bone marrow, including hematopoietic stem cells [HSC], were initially presumed to contribute to FSMCs, and to continuously replenish the mesenchymal pool as part of normal tissue homeostasis; however it has been shown that HSCs in a variety of tissues only give rise to blood cells and platelets.

The mesothelium is an epithelial monolayer that lines the vertebrate's coelomic cavities and internal organs. The mesothelium provides a non-adhesive layer that facilitates the frictionless movements of organs within the coelomic cavity, through the secretion of phospholipids and their entrapment via abundant microvilli present on the serosal side, and protects the serosal surfaces from abrasion, infection, and tumor dissemination. By synthesizing and secreting a plethora of cytokines, chemokines and growth factors, the mesothelium reportedly performs many functions, including the control of fluid and solute transport, regulation of inflammation, hematopoiesis and wound healing.

The ability to manipulate tissue regeneration is of great interest for clinical and research purposes. Characterization of stem and progenitor cells having diverse development potential is therefore of great interest.

PRIOR PUBLICATIONS

Mikawa and Gourdie (1996) *Dev. Biol.* 174, 221-232; J. Manner (1999) *Anat. Rec.* 255, 212-226; Wessels and Perez-Pomares (2004) Anat. Rec. A Discov. Mol. Cell. Evol. Biol. 276, 43-57; Smart et al. (2011) *Nature.* 474, 640-644; Cai et al. (2008) *Nature* 454, 104-108; Zhou et al. (2008) *Nature.* 454, 109-113; Chong et al. (2011) *Cell Stem Cell.* 9, 527-540; Carmona et al. (2011) J Cell Mol. Med. 15(5): 1200-9.

SUMMARY OF THE INVENTION

Compositions and methods are provided relating to the isolation and use of a fibroblast smooth muscle cell (FSMC) progenitor, which progenitor cell is committed to fibroblasts and smooth muscle of the internal organs, and their vasculature. The progenitor cells of the invention can be prospectively isolated from the mesothelium of fetal, embryonic or adult mammalian tissues. The progenitor cells are characterized as expressing methothelin (MSLN), and lacking expression of lineage markers associated with endothelial and eryhtroid lineages, which progenitor cells may be referred to herein as MSLN$^+$Lin$^-$.

The progenitor cells of the invention give rise to both smooth muscle cells and to fibroblasts in vivo and in vitro. The differentiated progeny of the MSLN$^+$Lin$^-$ cells have one or more of contractile stress bundles, alpha-smooth muscle-actin protein, vimentin, fibroblast-specific protein-1 (FSP1) and CD90, which markers that are associated with smooth muscle/fibroblast outcomes. The differentiated progeny also secrete proteins associated with smooth muscle/fibroblast outcomes, including type I collagen, type IV collagen and fibronectin.

Populations enriched for FSMC progenitors may be obtained by selection on the basis of expression of specific cell surface markers. The FSMC progenitors are characterized as being MSLN$^+$, and may further be characterized as lacking expression of one or more of the lineage markers Tie2, CD31, CD45, and Ter119. MSLN+Lin− cells have a unique surface phenotype, with markers associated with a mesenchymal nature including Thy1$^{high}$ (CD90), CD34$^{high}$, CD44$^{low}$ and CD105$^{low}$.

The progenitor cells are useful in transplantation, particularly for the regeneration of smooth muscle cells and fibroblasts; and the like. The cells are also useful for experimental evaluation, and as a source of lineage and cell specific products, including mRNA species useful in identifying genes specifically expressed in these cells, and as targets for the discovery of factors or molecules that can affect them. In vitro and in vivo systems are provided for the growth and analysis, including clonal analysis, of FSMCs.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE SPECIFIC EMBODIMENTS

Figure 1:
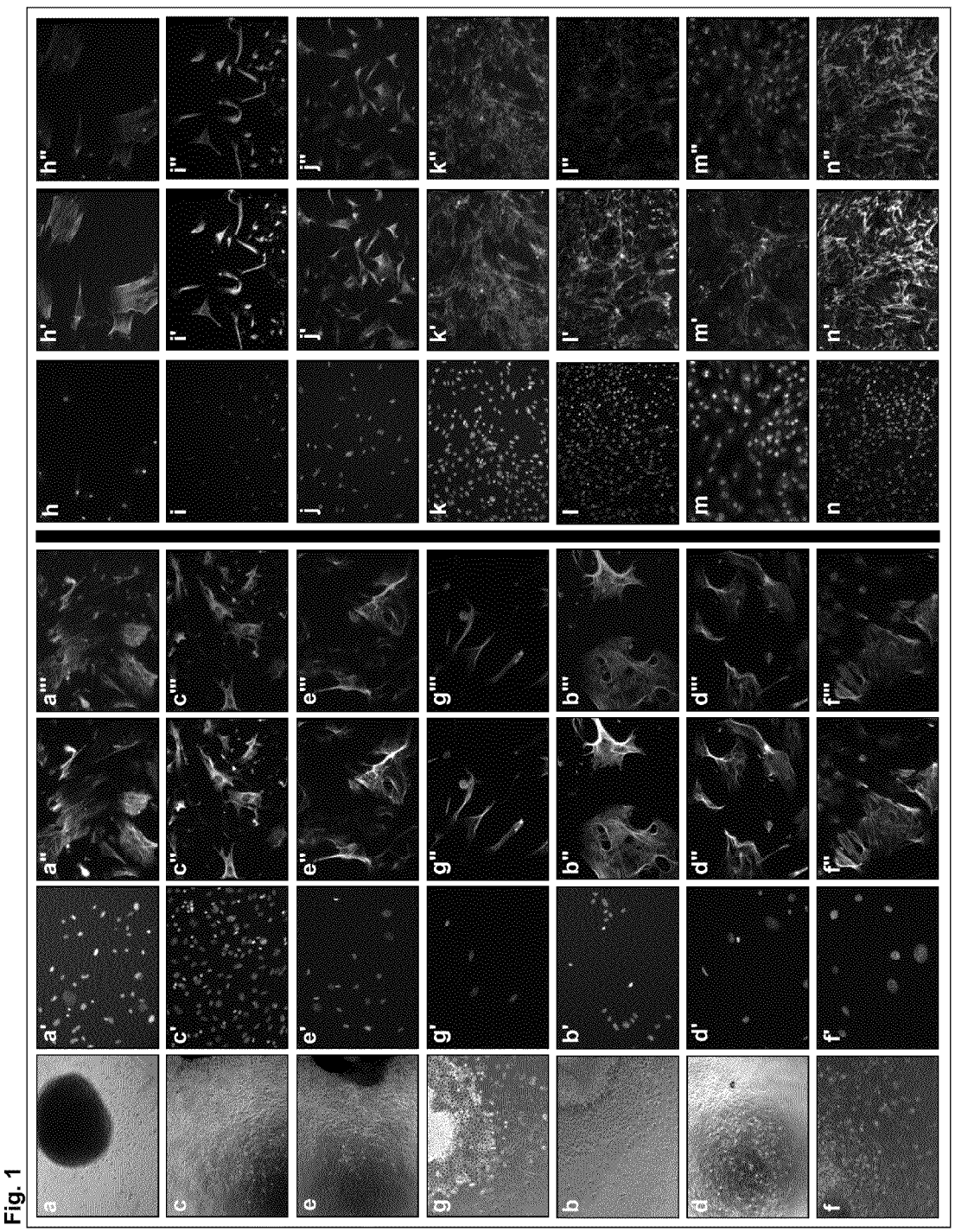
FIG. 1. Derivation of FSMCs from cultured mesothelium. Liver (a-a'''), spleen (b-b'''), kidney (cc'''), lung (d-d'''), intestine (e-e'''), mesentery (f-f'''), diaphragm (g-g'''). Bright field (a-g), nuclear DAPI staining (a'-g', h-n). Mesothelium-derived cells express α-SMA (a''-g'', hh''), Vimentin (i-i''), FSP1 (j-j''), CD90 (k-k''), Collagen type I (l-l''), Collagen type IV (m-m'') and Fibronectin (n-n''). Merged images (a'''-g''', h''-n'', DAPI is red, α-SMA is green except h'', l'', m''). Original magnifications ·20 (a-n).

Fibroblasts and smooth muscle cells (FSMCs) are principal cell types of connective and adventitial tissues that participate in the development, physiology and pathology of internal organs, with incompletely defined cellular origins. Provided herein are isolated cell populations in a committed lineage to FSMCs from the mesothelium, an epithelial monolayer covering the mammalian thoracic and abdominal cavities and internal organs. By targeting mesothelin (MSLN), a surface marker expressed on mesothelial cells, the progenitor cells can be identified and isolated. Using a genetic lineage tracing approach it is shown that mesothelium represents a common lineage to trunk FSMCs and trunk vasculature. The isolation of FSMC precursors enables examination of multiple aspects of smooth muscle and fibroblast biology as well as the isolation of these precursors for regenerative medicine purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "an", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

FSMC Progenitors. As used herein, the term FSMC progenitor is used to refer to cells that are isolated from mesothelium and that give rise to smooth muscle and firboblasts. The progenitor cells of the invention can be prospectively isolated from the mesothelium of fetal, embryonic or adult mammalian tissues. The progenitor cells are characterized as expressing methothelin (MSLN), and lacking expression of lineage markers associated with endothelial and eryhtroid lineages, which progenitor cells may be referred to herein as MSLN$^+$ Lin$^-$.

Populations enriched for FSMC progenitors may be obtained by selection on the basis of expression of specific cell surface markers. The FSMC progenitors are characterized as being MSLN$^+$, and may further be characterized as lacking expression of one or more of the lineage markers Tie2, CD31, CD45, and Ter119. MSLN$^+$Lin$^-$ cells have a unique surface phenotype, with markers associated with a mesenchymal nature including Thy1$^{high}$ (CD90), CD34$^{high}$, CD44$^{low}$ and CD105$^{low}$.

Smooth Muscle Cells. Smooth muscle is an involuntary non-striated muscle. Smooth muscle is found within the walls of blood vessels such as in the tunica media layer of large and small arteries, arterioles and veins. Smooth muscle is also found in lymphatic vessels, the urinary bladder, uterus, male and female reproductive tracts, gastrointestinal tract, respiratory tract, arrector pili of skin, the ciliary muscle, and iris of the eye. The structure and function is basically the same in smooth muscle cells in different organs, but the inducing stimuli differ substantially. Smooth muscle is fundamentally different from skeletal muscle and cardiac muscle in terms of structure, function, regulation of contraction, and excitation-contraction coupling.

Smooth muscle fibers have a fusiform shape and, like striated muscle, can tense and relax. However, smooth muscle containing tissue tend to demonstrate greater elasticity and function within a larger length-tension curve than striated muscle. A substantial portion of the volume of the cytoplasm of smooth muscle cells are taken up by the Myosin II and actin (SMA). Smooth muscle does not contain the protein troponin; instead calmodulin, caldesmon and calponin are expressed. Tropomyosin is present in smooth muscle, spanning seven actin monomers and is laid out end to end over the entire length of the thin filaments.

Muscle regeneration as used herein refers to the process by which new muscle forms from muscle progenitor cells. A therapeutic composition will usually confer an increase in the number of new fibers by at least 1%, more preferably by at least 20%, and most preferably by at least 50%. The growth of muscle may be measured by an increase in wet weight, an increase in protein content, an increase in the number of muscle fibers; etc.

Muscle regeneration may also be monitored by the mitotic index of muscle. For example, cells may be exposed to a labeling agent for a time equivalent to two doubling times. The mitotic index is the fraction of cells in the culture which have labeled nuclei when grown in the presence of a tracer which only incorporates during S phase (i.e., BrdU) and the doubling time is defined as the average S time required for the number of cells in the culture to increase by a factor of two. The survival of muscle fibers may refer to the prevention of loss of muscle fibers as evidenced by necrosis or apoptosis or the prevention of other mechanisms of muscle fiber loss. Muscles can be lost from injury, disease, and the like.

Fibroblasts form the structural framework (stroma) for animal tissues, and plays a critical role in wound healing. Fibroblasts are morphologically heterogeneous with diverse appearances depending on their location and activity. The main function of fibroblasts is to maintain the structural integrity of connective tissues by continuously secreting precursors of the extracellular matrix. Fibroblasts secrete the precursors of all the components of the extracellular matrix, primarily the ground substance and a variety of fibers. The composition of the extracellular matrix determines the physical properties of connective tissues.

Fibroblasts have a branched cytoplasm surrounding an elliptical, speckled nucleus having one or two nucleoli. Active fibroblasts can be recognized by their abundant rough endoplasmic reticulum. Inactive fibroblasts are smaller and spindle shaped. They have a reduced rough endoplasmic reticulum. Fibroblasts make collagens, glycosaminoglycans, reticular and elastic fibers.

Mesothelium is a membrane that forms the lining of several body cavities: the pleura, peritoneum and pericardium.

Mesothelium that covers the internal organs is called visceral mesothelium, while the layer that covers the body walls is called the parietal mesothelium. The mesothelium forms a monolayer of flattened squamous-like epithelial cells resting on a thin basement membrane supported by dense irregular connective tissue. The luminal surface is covered with microvilli. The proteins and serosal fluid trapped by the microvilli provide a frictionless surface for internal organs to slide past one another.

Mesothelin. (MSLN) is a 40 kDa protein present on normal mesothelial cells and overexpressed in several human tumors, including mesothelioma and ovarian and pancreatic adenocarcinoma, Genbank accession number for the human protein is D49441. The mesothelin gene encodes a precursor protein that is processed to yield mesothelin, which is attached to the cell membrane by a glycophosphatidylinositol linkage and a 31-kDa shed fragment named megakaryocyte-potentiating factor (MPF). See, for example, Kojima et al. (1995) J. Biol. Chem. 270 (37): 21984-90, and Chang et al. (1996) Proc. Natl. Acad. Sci. U.S.A. 93 (1): 136-40.

Positive and Negative Staining. The subject FSMC progenitor cells are characterized by their expression of cell surface markers. While it is commonplace in the art to refer to cells as "positive" or "negative" for a particular marker, actual expression levels are a quantitative trait. The number of molecules on the cell surface can vary by several logs, yet still be characterized as "positive". It is also understood by those of skill in the art that a cell which is negative for staining, i.e. the level of binding of a marker specific reagent is not detectably different from a control, e.g. an isotype matched control; may express minor amounts of the marker. Characterization of the level of staining permits subtle distinctions between cell populations.

The staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

In order to normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining above the brightness of an isotype matched control, but it is not as intense as the most brightly staining cells normally found in the population. Low positive cells may have unique properties that differ from the negative and brightly stained positive cells of the sample. An alternative control may utilize a substrate having a defined density of marker on its surface, for example a fabricated bead or cell line, which provides the positive control for intensity.

Sources of Progenitor Cells. Ex vivo and in vitro cell populations useful as a source of cells may include fresh or frozen mesothelium obtained from embryonic, fetal, pediatric or adult tissue. The methods can include further enrichment or purification procedures or steps for cell isolation by positive selection for other cell specific markers. The progenitor cells may be obtained from any mammalian species, e.g. human, equine, bovine, porcine, canine, feline, rodent, e.g. mice, rats, hamster, primate, etc.

Markers. The markers for selection of FSMC progenitors and/or BM derived myogenic cells will vary with the specific cells. As described above, a number of well-known markers can be used for positive selection and negative selection. A useful markers for positive selection is MSLN. Useful markers for negative selection may include, without limitation, one, two or more of: Tie2, CD31, CD45, and Ter119. MSLN$^+$ Lin$^-$ cells have a unique surface phenotype, with markers associated with a mesenchymal nature including Thy1$^{high}$ (CD90), CD34$^{high}$, CD44$^{low}$ and CD105$^{low}$ and may be selected for one or more of these markers.

Specific Binding Member. The term "specific binding member" or "binding member" as used herein refers to a member of a specific binding pair, i.e. two molecules, usually two different molecules, where one of the molecules (i.e., first specific binding member) through chemical or physical means specifically binds to the other molecule (i.e., second specific binding member). The complementary members of a specific binding pair are sometimes referred to as a ligand and receptor; or receptor and counter-receptor. Such specific binding members are useful in positive and negative selection methods. Specific binding pairs of interest include carbohydrates and lectins; complementary nucleotide sequences; peptide ligands and receptor; effector and receptor molecules; hormones and hormone binding protein; enzyme cofactors and enzymes; enzyme inhibitors and enzymes; antibodies and antigens; etc. The specific binding pairs may include analogs, derivatives and fragments of the original specific binding member. For example, a receptor and ligand pair may include peptide fragments, chemically synthesized peptidomimetics, labeled protein, derivatized protein, etc.

Especially useful reagents are antibodies specific for markers present on the desired cells (for positive selection) and undesired cells (for negative selection). Whole antibodies may be used, or fragments, e.g. Fab, F(ab')$_2$, light or heavy chain fragments, etc. Such selection antibodies may be polyclonal or monoclonal and are generally commercially available or alternatively, readily produced by techniques known to those skilled in the art. Antibodies selected for use will have a low level of non-specific staining and will usually have an affinity of at least about 100 µM for the antigen.

In one embodiment of the invention, antibodies for selection are coupled to a label. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red, cy7, cy5. Frequently each antibody is labeled with a different fluorochrome, to permit independent sorting for each marker. The exact method for coupling to a label is not critical to the practice of the invention, and a number of alternatives are known in the art. Direct coupling attaches the antibodies to the label. Indirect coupling can be accomplished by several methods. The antibodies may be coupled to one member of a high affinity binding system, e.g. biotin, and the particles attached to the other member, e.g. avidin. One may also use second stage antibodies that recognize species-specific epitopes of the antibodies, e.g. anti-mouse Ig, anti-rat Ig, etc. Indirect coupling methods allow the use of a single labeled entity, e.g. antibody, avidin, etc., with a variety of separation antibodies.

Enrichment Methods

The subject FSMC progenitors are separated from a complex mixture of cells by techniques that enrich for cells having the characteristics as described. For example, a mesothelium sample may initially be prepared by dissociation. From this population, cells may be selected for expression of MSLN; and negatively selected for lineage markers as described above.

Dissociation of tissue may include digestion with a suitable protease, e.g. collagenase, dispase, etc. An appropriate solution is used for dispersion or suspension. Such solution will generally be a balanced salt solution, e.g. normal saline, PBS, Hanks balanced salt solution, etc., supplemented with fetal calf serum or other naturally occurring factors, in conjunction with an acceptable buffer at low concentration, generally from 5-25 mM. Convenient buffers include HEPES, phosphate buffers, lactate buffers, etc.

Separation of the subject cell population will then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (propidium iodide, 7-AAD). Any technique may be employed which is not unduly detrimental to the viability of the selected cells.

The affinity reagents may be specific receptors or ligands for the cell surface molecules indicated above. The details of the preparation of antibodies and their suitability for use as specific binding members are well known to those skilled in the art. Of particular interest is the use of antibodies as affinity reagents.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium which maintains the viability of the cells. A preferred medium is phosphate buffered saline containing from 0.1 to 0.5% BSA. Various media are commercially available and may be used according to the nature of the cells, including Dulbeccos Modified Eagle Medium (dMEM), Hank's Basic Salt Solution (HBSS), Dulbeccos phosphate buffered saline (dPBS), RPMI, Iscoves medium, PBS with 5 mM EDTA, etc., frequently supplemented with fetal calf serum, BSA, HSA, etc.

The labeled cells are then separated as to the phenotype described above. The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscoves medium, etc., frequently supplemented with fetal calf serum.

Compositions highly enriched for FSMC activity are achieved in this manner. The subject population will be at or about 50% or more of the cell composition, and usually at or about 80%, 85%, 90% or more of the cell composition, and may be as much as about 95% or more of the live cell population. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. Once thawed, the cells may be expanded by use of growth factors and/or feeder cells for proliferation and differentiation.

The compositions thus obtained have a variety of uses in clinical therapy, research, development, and commercial purposes. For therapeutic purposes, for example, FSMC progenitors may be administered to enhance tissue maintenance or repair of muscle for any perceived need, such as an inborn error in metabolic function, the effect of a disease condition, or the result of significant trauma.

To determine the suitability of cell compositions for therapeutic administration, the cells can first be tested in a suitable animal model. At one level, cells are assessed for their ability to survive and generate the desired phenotype in vivo. Cell compositions may be administered to immunodeficient animals (such as nude mice, or animals rendered immunodeficient chemically or by irradiation). Tissues are harvested after a period of regrowth, and assessed as to whether the administered cells or progeny thereof are still present.

This can be performed by administering cells that express a detectable label (such as green fluorescent protein, or β-galactosidase); that have been prelabeled (for example, with BrdU or [$^3$H] thymidine), or by subsequent detection of a constitutive cell marker (for example, using human-specific antibody). The presence and phenotype of the administered cells can be assessed by immunohistochemistry or ELISA using human-specific antibody, or by RT-PCR analysis using primers and hybridization conditions that cause amplification to be specific for human polynucleotides, according to published sequence data.

Cells may be genetically altered in order to introduce genes useful in the differentiated cell, e.g. repair of a genetic defect in an individual, selectable marker, etc. Cells may be genetically altering by transfection or transduction with a suitable vector, homologous recombination, or other appropriate technique, so that they express a gene of interest. In other embodiments, a selectable marker is introduced, to provide for greater purity of the desired cell. Cells may be genetically altered using vector containing supernatants over a 8-16 h period, and then exchanged into growth medium for 1-2 days. Genetically altered cells are selected using a drug selection agent such as puromycin, G418, or blasticidin, and then recultured. Genetically modified cells can also be selected for a detectable marker, e.g. GFP, etc., by cell sorting methods known in the art.

Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. Retrovirus based vectors have been shown to be particularly useful when the target cells are progenitor cells. For example, see Schwarzenberger et al. (1996) Blood 87:472-478; Nolta et al. (1996) P.N.A.S. 93:2414-2419; and Maze et al. (1996) P.N.A.S. 93:206-210.

Combinations of retroviruses and an appropriate packaging line may be used, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

Lentiviral vectors such as those based on HIV or FIV gag sequences can be used to transfect non-dividing cells, such as the resting phase of human stem cells (see Uchida et al. (1998) P.N.A.S. 95(20):11939-44).

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) *Mol. Cell. Biol.* 5:431-437); PA317 (Miller et al. (1986) *Mol. Cell. Biol.* 6:2895-2902) GRIP (Danos et al. (1988) *PNAS* 85:6460-6464). Retroviruses packaged with xenotropic envelope protein, e.g. AKR env, are capable of infecting most mammalian cell types, except murine cells.

The vectors may include genes that must later be removed, e.g. using a recombinase system such as Cre/Lox, or the cells that express them destroyed, e.g. by including genes that allow selective toxicity such as herpesvirus TK, bcl-xs, etc.

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in different cell types.

Therapeutic Methods

The FSMC progenitors may be used for tissue reconstitution or regeneration in a human patient or other subject in need of such treatment. The cells are administered in a manner that permits them to graft or migrate to the intended tissue site and reconstitute or regenerate the functionally deficient area.

The differentiating cells may be administered in any physiologically acceptable excipient, where the cells may find an appropriate site for regeneration and differentiation. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or feeder cells associated with progenitor cell proliferation and differentiation.

The cells of this invention can be supplied in the form of a pharmaceutical composition, comprising an isotonic excipient prepared under sufficiently sterile conditions for human administration. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells.

The subject methods are useful for both prophylactic and therapeutic purposes. Thus, as used herein, the term "treating" is used to refer to both prevention of disease, and treatment of a pre-existing condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. Evidence of therapeutic effect may be any diminution in the severity of disease. The therapeutic effect can be measured in terms of clinical outcome or can be determined by immunological or biochemical tests.

The dosage of the therapeutic formulation will vary widely, depending upon the nature of the condition, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, semi-weekly, or otherwise as needed to maintain an effective dosage level.

Libraries

The cells of this invention can be used to prepare a cDNA library relatively uncontaminated with cDNA preferentially expressed in cells from other lineages. For example, FSMC progenitors are collected by centrifugation at 1000 rpm for 5 min, and then mRNA is prepared from the pellet by standard techniques (Sambrook et al., supra). After reverse transcribing into cDNA, the preparation can be subtracted with cDNA from other progenitor cells, or end-stage cells from the myocyte or any other developmental pathway.

The cells of this invention can also be used to prepare antibodies that are specific for markers of FSMC and their precursors. Polyclonal antibodies can be prepared by injecting a vertebrate animal with cells of this invention in an immunogenic form. Production of monoclonal antibodies is described in standard references. Specific antibody molecules can also be produced by contacting a library of immunocompetent cells or viral particles with the target antigen, and growing out positively selected clones. See Marks et al., New Eng. J. Med. 335:730, 1996, and McGuiness et al., Nature Biotechnol. 14:1449, 1996. A further alternative is reassembly of random DNA fragments into antibody encoding regions, as described in EP patent application 1,094,108 A.

The antibodies in turn can be used to identify or rescue cells of a desired phenotype from a mixed cell population, for purposes such as containing during immunodiagnosis using tissue samples, and isolating precursor cells from terminally differentiated myocytes and cells of other lineages.

Of particular interest is the examination of gene expression in the FSMCs of the invention. The expressed set of genes may be compared against other subsets of cells, against other stem or progenitor cells, against adult muscle tissue, and the like, as known in the art. Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A+mRNA. One of skill in the art can readily use these methods to determine differences in the size or amount of mRNA transcripts between two samples.

Any suitable method for detecting and comparing mRNA expression levels in a sample can be used in connection with the methods of the invention. For example, mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al., *Science* (1995) 270:484). In short, SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific sequence delimiters (e.g., restriction enzyme sites) are used as unique identifiers of genes, coupled with information about fragment length or fragment location within the expressed gene. The relative representation of an expressed gene with a sample can then be estimated based on the relative representation of the fragment associated with that gene within the pool of all possible fragments. Methods and compositions for carrying out DD are well known in the art, see, e.g., U.S. Pat. No. 5,776,683; and U.S. Pat. No. 5,807,680.

Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Hybridization to arrays may be performed, where the arrays can be produced according to any suitable methods known in the art. For example, methods of producing large arrays of oligonucleotides are described in U.S. Pat. Nos. 5,134,854, and 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Methods for collection of data from hybridization of samples with an array are also well known in the art. For example, the polynucleotides of the cell samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., *Genome Res.* (1996) 6:639. A scan, using the appropriate excitation line, is performed for each fluorophore used. The digital images generated from the scan are then combined for subsequent analysis. For any particular array element, the ratio of the fluorescent signal from one sample is compared to the fluorescent signal from another sample, and the relative signal intensity determined.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

Pattern matching can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

In another screening method, the test sample is assayed for the level of polypeptide of interest. Diagnosis can be accomplished using any of a number of methods to determine the absence or presence or altered amounts of a differentially expressed polypeptide in the test sample. For example, detection can utilize staining of cells or histological sections (e.g., from a biopsy sample) with labeled antibodies, performed in accordance with conventional methods. Cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.) The absence or presence of antibody binding can be determined by various methods, including flow cytometry of dissociated cells, microscopy, radiography, scintillation counting, etc. Any suitable alternative methods can of qualitative or quantitative detection of levels or amounts of differentially expressed polypeptide can be used, for example ELISA, western blot, immunoprecipitation, radioimmunoassay, etc.

Screening Assays

The cells are also useful for in vitro assays and screening to detect factors that are active on cells of the FSMC lineage. Of particular interest are screening assays for agents that are active on human cells. A wide variety of assays may be used for this purpose, including immunoassays for protein binding; determination of cell growth, differentiation and functional activity; production of factors; and the like.

In screening assays for biologically active agents, viruses, etc. the subject cells, usually a culture comprising the subject cells, is contacted with the agent of interest, and the effect of the agent assessed by monitoring output parameters, such as expression of markers, cell viability, and the like. The cells may be freshly isolated, cultured, genetically altered as described above, or the like. The cells may be environmentally induced variants of clonal cultures: e.g. split into independent cultures and grown under distinct conditions, for example with or without virus; in the presence or absence of other cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents, such as viruses, candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1:1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) *Trends Biotechnol.* 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) *Biotechniques* 26(1):112-225; Kawamoto et al. (1999) *Genome Res* 9(12):1305-12; and Chen et al. (1998) *Genomics* 51(3):313-24, for examples.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXPERIMENTAL

Example 1

Fibroblasts and smooth muscle cells (FSMCs) are principal cell types of connective and adventitial tissues that participate in the development, physiology and pathology of internal organs, with incompletely defined cellular origins. Here, we identify a committed lineage to FSMCs in the mesothelium, an epithelial monolayer covering the mammalian thoracic and abdominal cavities and internal organs, and prospectively isolate their precursors. Time-lapse imaging and transplantation experiments reveal robust generation of FSMCs from the mesothelium. By targeting Mesothelin (MSLN), a surface marker expressed on mesothelial cells, we identify and isolate precursors capable of generating FSMCs. Using a genetic lineage tracing approach, we show that embryonic mesothelium represents a common lineage to trunk FSMCs, and trunk vasculature, with minimal contributions from neural crest, or circulating cells. The isolation of FSMC precursors enables examination of multiple aspects of smooth muscle and fibroblast biology as well as the prospective isolation of these precursors for regenerative medicine purposes.

Results

Derivation of FSMCs from the Mesothelium.

Small mesothelial tissues were removed from the surfaces of the liver, spleen, kidney, lung, intestine, mesentery, diaphragm and peritoneal wall of adult mice, and cultured on tissue culture plates. These patches of tissue were enriched for, but not entirely composed of mesothelial cells. Following the attachments of the mesothelium to the culture plates, fibroblasts/smooth muscle cells (FSMCs) emerged, abundantly, from all of the tissue's peripheries (FIG. 1, a-h), and were absent only in regions where attachment of the mesothelium to the culture dish was poor. FSMCs displayed a spindle shape or a flattened morphology with filopodia/lamellipodia, consistent with a mesenchymal nature (FIG. 1, a'''-g''') and reached culture confluence within several days.

FSMCs from all cultured organs, displayed contractile stress bundles, expressed alpha-Smooth Muscle-Actin protein ($\alpha$-SMA; FIG. 1, a'''-h'''), Vimentin (FIG. 1, i-i'') Fibroblast-Specific Protein-1 (FSP1; FIG. 1, j-j'') and Thy1 protein (CD90; FIG. 1, k-k''), markers that are associated with smooth muscle/fibroblast outcomes (FIG. 1b). FSMCs and the culture plates on which they where grown immunostained for Type I Collagen (FIG. 1, ll"), Type IV Collagen (FIG. 1, m-m") and Fibronectin (FIG. 1, n-n"), showing their ability in-vitro to express and secrete components of the extra-cellular matrix.

Time-lapse video was used to capture the dynamic processes of FSMC formation from cultured mesothelial tissues. Following the attachment of mesothelium to the culture plate, FSMCs emerged at the leading edges of the explants from numerous peripheral sites. Emerging FSMCs displayed a spindle-shape or a flattened morphology and were highly motile within the culture dishes, continuously forming filopodia and lamelipodia in the direction of their migration. In some instances, contractile forces from newly emerging FSMCs at leading edge sites of the tissue, led to pulling of the tissue explants along the culture plates. FSMCs did not exhibit directed movement, but rather sampled the tissue culture plates, continuously changing their direction of migration.

Figure 2:
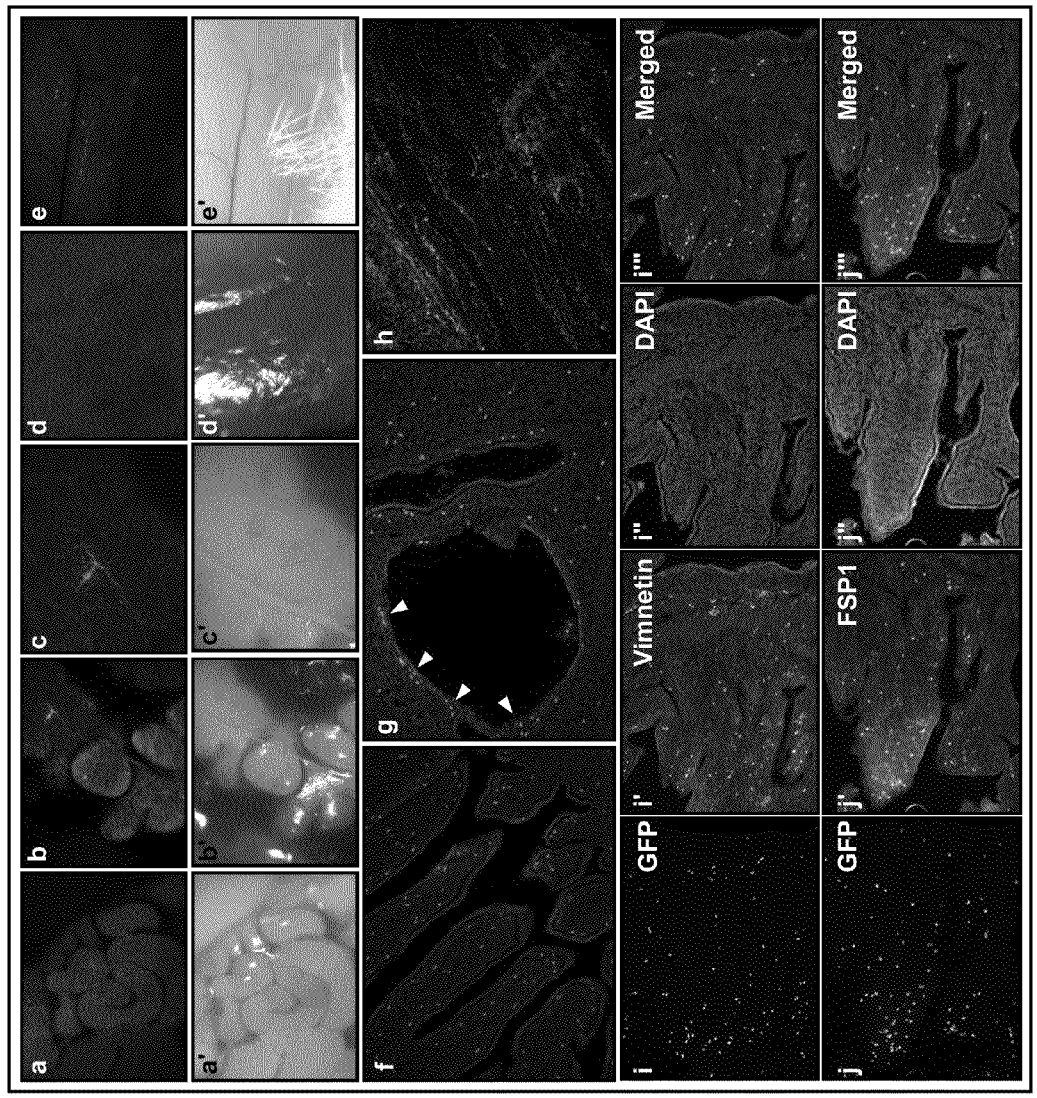
FIG. 2. Derivation of FSMCs from transplantation of mesothelium in vivo. Representative images of the abdominal cavity, from mice three months post transplantation of mesothelium. Lower digestive system (a-c), liver (d) and peritoneum (e). Sections through the lower digestive system (f, g) and peritoneum (h) showing FSMCs and cell foci along a vessel opening (g, white arrowheads). Immunohistochemistry of Vimentin (ii''') and FSP1 (j-j'''), showing co-localization of the FSMCs markers with graft-derived GFP+ cells. Original magnifications: ·10 (a, b, f, i, j), ·20 (c-e, g, h).

To test the in-vivo potential of the adult mesothelium to generate FSMCs, small (<1 mm$^2$) explants of adult mesothelium were harvested from transgenic mice expressing the enhanced green fluorescent protein under the Actin promoter (Actin-eGFP), from mesentery, peritoneum or kidney. Tissues were then transplanted separately, into adult Rag(−/−) gamma chain(−/−) mice (to prevent tissue rejection), underneath the mesothelium covering the small intestine, liver or peritoneal wall (see methods). Host mice were sacrificed three months post transplantation and the abdominal cavity was exposed and analyzed for any presence of donor-derived cells. GFP$_+$ cells were found along the lower digestive system, liver and peritoneum, in areas remote from the site of transplantation (FIG. 2, a-e).

Tissues and organs were harvested and processed for histology. Within the lower digestive system, GFP$_+$ cells with a mesenchymal morphology occupied subepithelial and stromal regions of the digestive system (FIG. 2, f, g). We also found individual GFP$_+$ cells and cell foci along blood vessels' media and adventitia (FIG. 2g, white arrowheads). In the peritoneum where a small patch of mesothelium tissue was transplanted, individual GFP$_+$ cells were scattered throughout and in-between muscle fibers (FIG. 2h). We did not find any contribution of GFP$_+$ cells to the organ parenchyma, or to other cell or tissue types within the examined organs, including the mesothelium, except for a single case in which a GFP$_+$ mesothelium appeared at the site of transplantation. Instead, GFP$_+$ cells ubiquitously displayed mesenchymal morphology, and expressed markers associated with FSMCs, including Vimentin protein (FIG. 2, i-i''') and FSP1 (FIG. 2, j-j'''), within most sites examined.

Mesothelin (MSLN) is a Novel Marker of FSMC Precursors.

Figure 7:
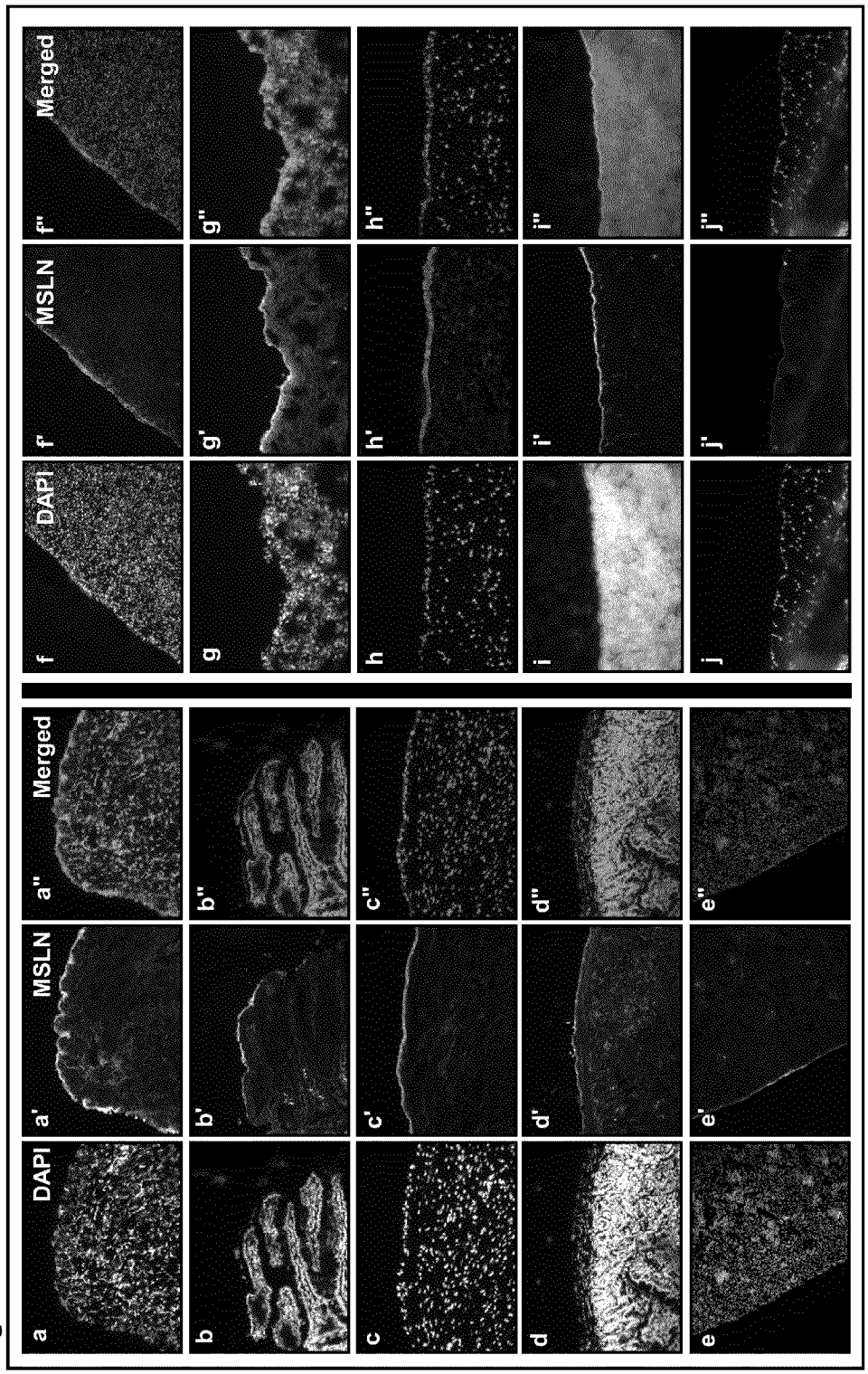
FIG. 7. Mesothelin (MSLN) protein is expressed on the mesothelium covering the visceral and parietal tissues and organs. MSLN is ubiquitously expressed within the mesothelial tissue surrounding the bladder (a-a''), intestine (b-b''), heart (c-c''), stomach (d-d''), spleen (ee''), liver (f-f''), lung (g-g''), mesentery (h-h''), thymus (i-i'') and peritoneum (j-j'').

Because the mesothelium transplants described above were not a pure population of mesothelial cells, we looked for ways to follow only cells derived from mesothelium. Mesothelin (MSLN) is a 40-kDa membrane glycoprotein that is present on normal mesothelium and is over-expressed in a subset of cells in several human tumors, including mesothelioma. MSLN protein labeled the adult mesothelium covering the internal organs, including the heart epicardium, lungs, spleen, thymus, kidney, liver, small and large intestine, stomach, mesentery and bladder, and on the parietal mesothelium, including the diaphragm (FIG. 7, a-j).

Figure 8:
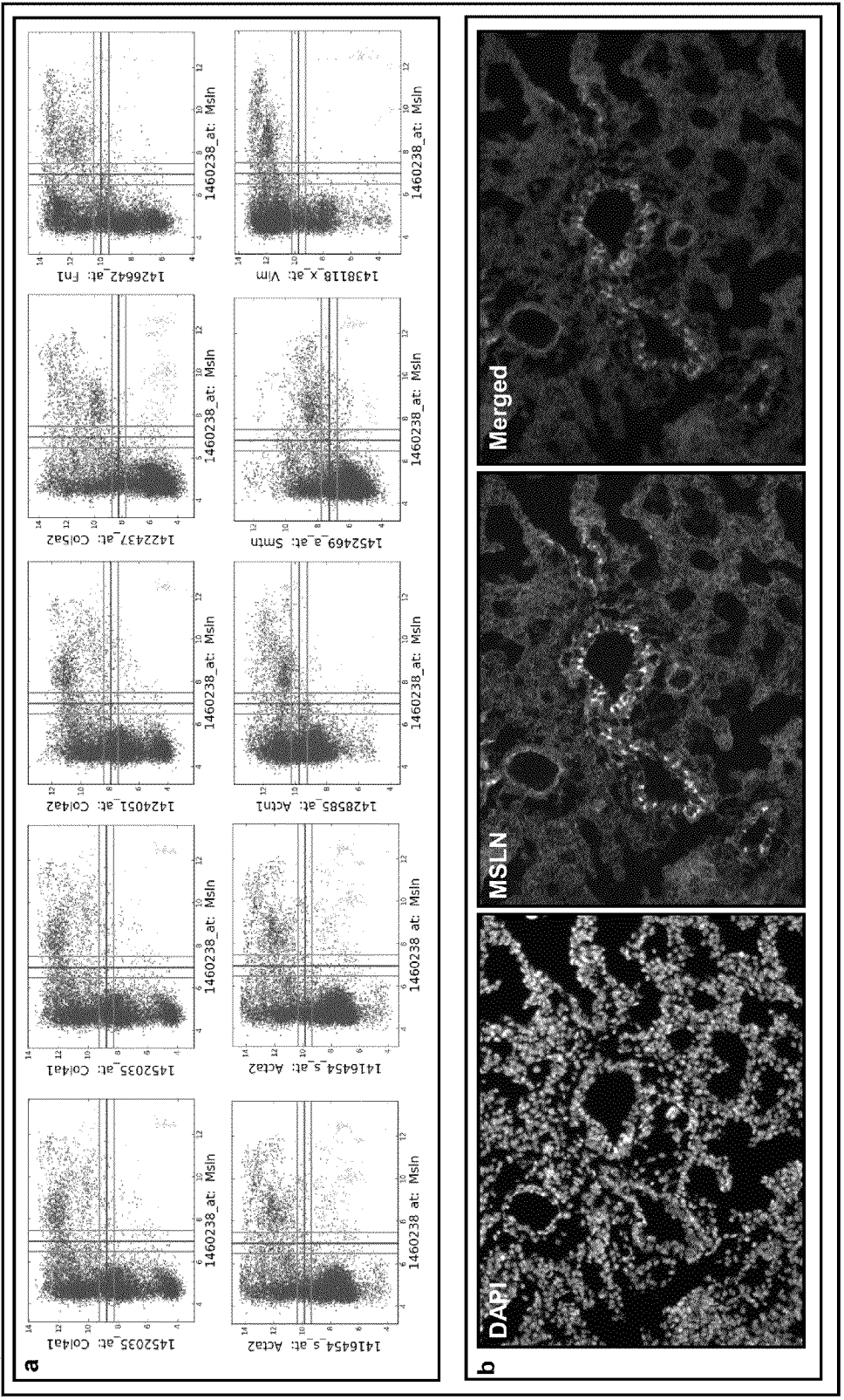
FIG. 8. Boolean relationships of MSLN. (a) Each dot represents a boolean relationship of Mesothelin (MSLN) on a single Affymetrix 430 2.0 mouse array from NCBI's Gene Expression Omnibus showing all tissues in red, and adult mouse lung in blue. X-axis represents Mesothelin expression within the specific arrays, Y-axis represents the expression of each specific other marker. A high-to-high Boolean relationship exists between MSLN and Type 4A1 Collagen (Col4a1), Type 4A2 Collagen (Col4a2), Type 5A2 Collagen (Col5a2), Fibronectin 1 (Fn1), alpha2-smooth muscle actin-aorta (Acta2), alpha1-smooth muscle actinin (Actn1) and Smoothelin (Smtn) and Vimentin (Vim). Light blue dots represent boolean relationships of MSLN on arrays from adult mouse lung epithelium, which most likely is separate from the FSMC lineage. (b) Adult mouse airway epithelium express MSLN protein, separate from the FSMC lineage. Original magnifications: ·20 (b).

We used an independent, non-biased approach to ask whether MSLN expression could be used as a marker for FSMCs precursors by looking at the Boolean relationships of MSLN. Using a Boolean algorithm on 10,823 Affymetrix 430 2.0 mouse arrays that were downloaded from NCBI's Gene Expression Omnibus, MSLN message showed significant high-to-high relationships with known FSMC markers (FIG. 8a), including Vimentin, alpha2-smooth muscle actin-aorta, alpha1-smooth muscle actinin and Smoothelin as well as structural genes of the ECM, including Fibronectin, Fibrillin, Col4A1, Col4A2, Col4A5 and Col5A2, implying in silico that MSLN expression is highly associated with a smooth muscle/fibroblast lineage.

Figure 3A:
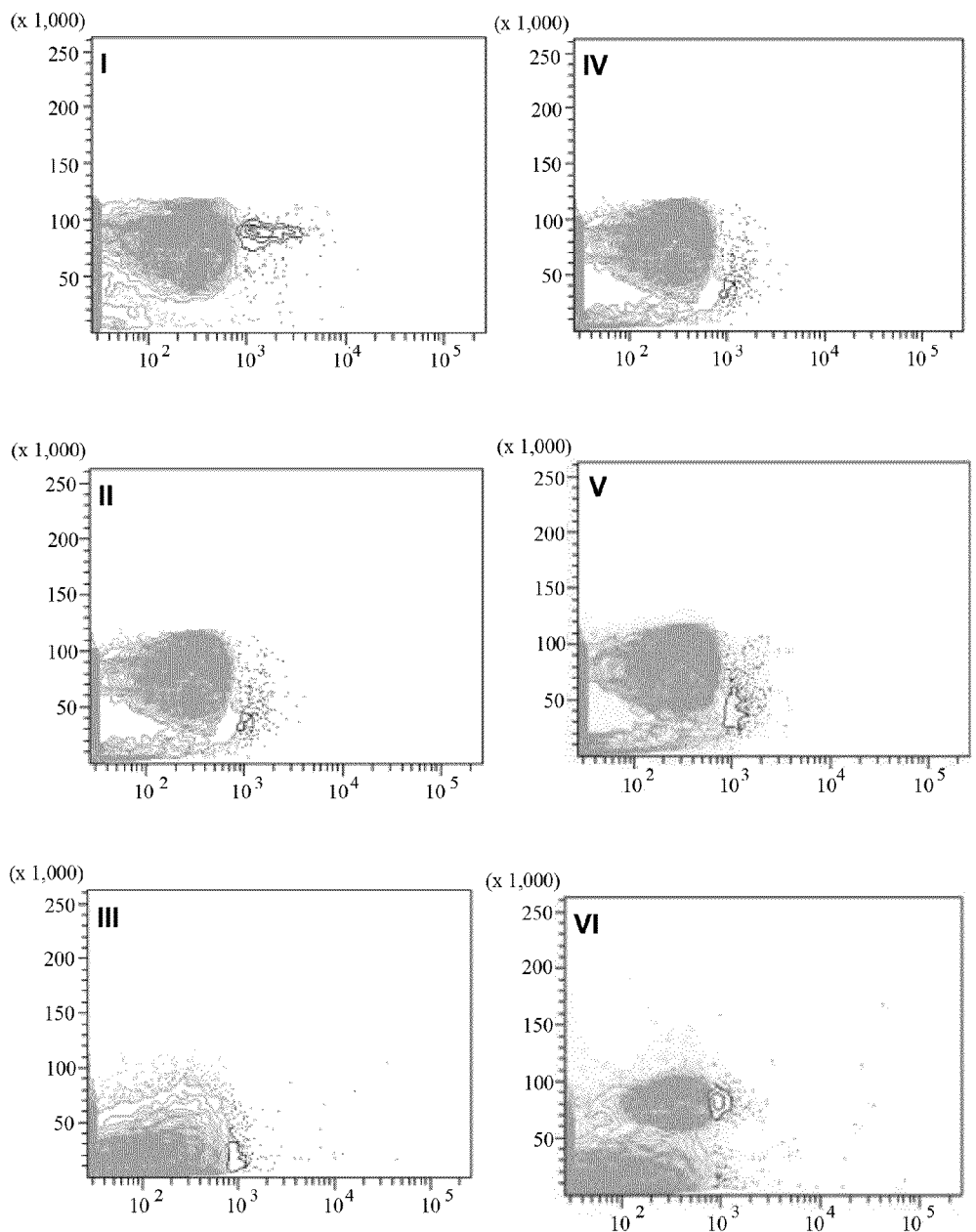
FIG. 3. Flow cytometry of MSLN+Lin− cells. (a) X-axis represents MSLN expression, Y-axis represents side scatter. A population of cells characterized by MSLN+Lin− is present within the heart (I), lung (II), liver (III), peritoneal wall (IV), kidney (V), and thymus (VI). (b) MSLN+Lin− cells express a surface profile associated with a mesenchymal nature. Blue is IgG control, red is antibody. Following their isolation by flow cytometry, 16 cultured MSLN+Lin− form cell foci (c). Cells at the periphery adopt a mesenchymal nature and express MSLN (d), Vimentin (e), FSP1 (f), Type I Collagen (g), Type IV (h) and α-SMA (i) proteins. DAPI (d'-i'). Merged (d''-i'', DAPI in blue, antibody in red). Original magnifications: ·20 (c-i).
Figure 3B:
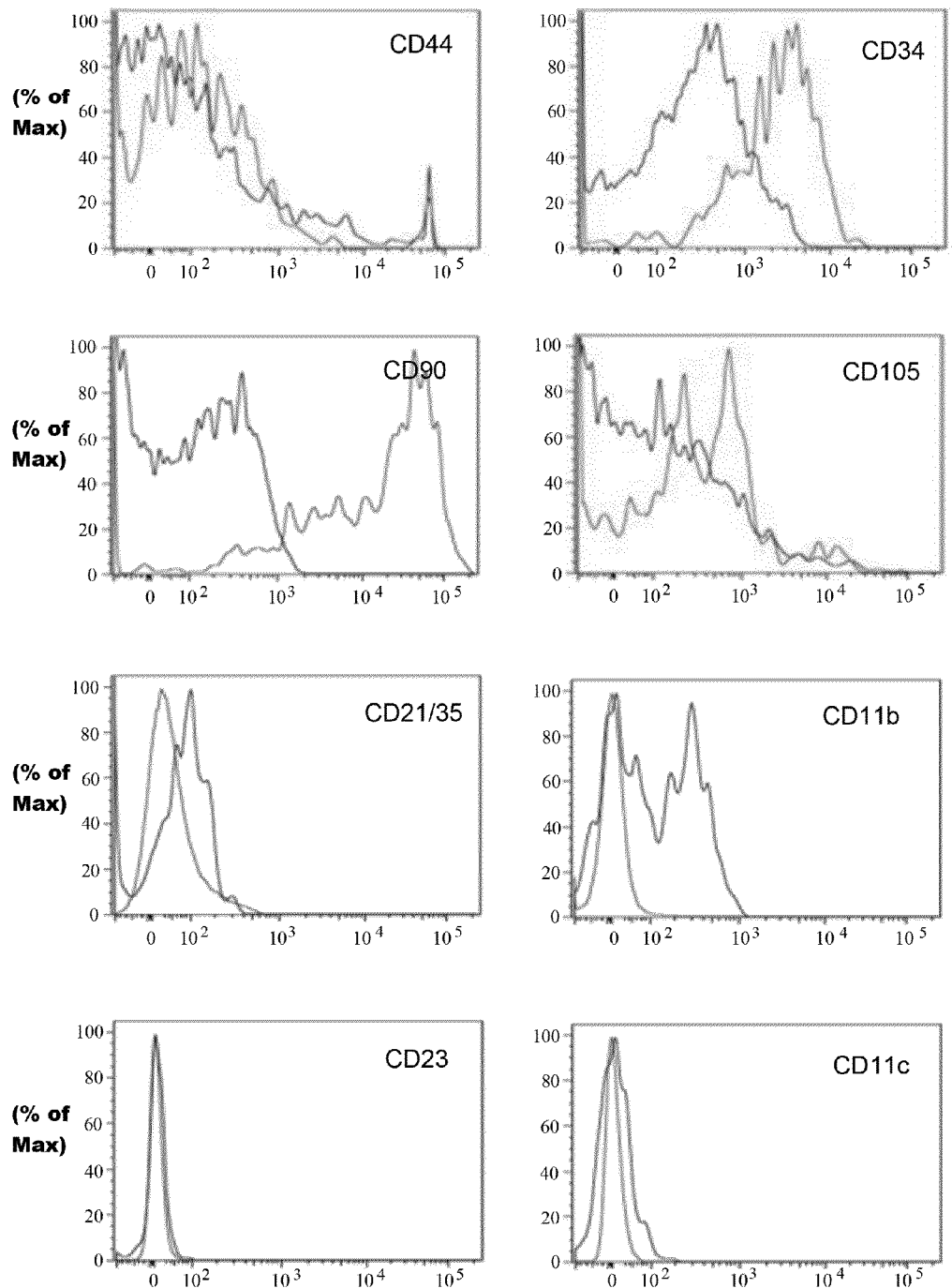

Flow cytometry was then used to isolate FSMC precursors by gating on the absence of Tie2, PECAM-1/CD31 (for endothelial cells), CD45, Ter119 (for blood cells), and presence of MSLN, herein referred to as MSLN$^+$Lin$^-$. A MSLN$^+$Lin$^-$ population was present within all adult visceral organs tested including heart, lung, liver, peritoneal wall, kidney, and thymus (FIG. 3a) and was represented in extremely low numbers within total viable cells (0.2%-0.4%). MSLN$^+$Lin$^-$ cells expressed a unique surface phenotype, with markers associated with a mesenchymal nature (FIG. 3b), including Thy1$^{high}$ (CD90), CD34$^{high}$, CD44$^{low}$ and CD105$^{low}$, with a mean fluorescent intensity (MFI) of 31,893 (for CD90), 2,294 (for CD34), 52 (for CD44) and 27 (for CD105).

Using flow cytometry, MSLN$^+$Lin$^-$ cells were sorted from the internal organs of postnatal day 1 (P1) mice and cultured in-vitro. Following their culturing, MSLN$^+$Lin$^-$ cells formed cell foci within several days (FIG. 3c), which expanded throughout subsequent culture days. At the periphery of each focus, cells acquired fibroblast/smooth muscle morphologies and gradually emerged from the focus as single motile cells. Subsequently, numerous FSMCs appeared within the culture dish that expressed Mesothelin (FIG. 3, d-d"), Vimentin (FIG. 3, e-e"), FSP1 (FIG. 3, f-f"), Type I Collagen (FIG. 3, g-g"), Type IV Collagen (FIG. 3, HH") and α-SMA (FIG. 3, i-i"), within all cultured cells.

Figure 4A:
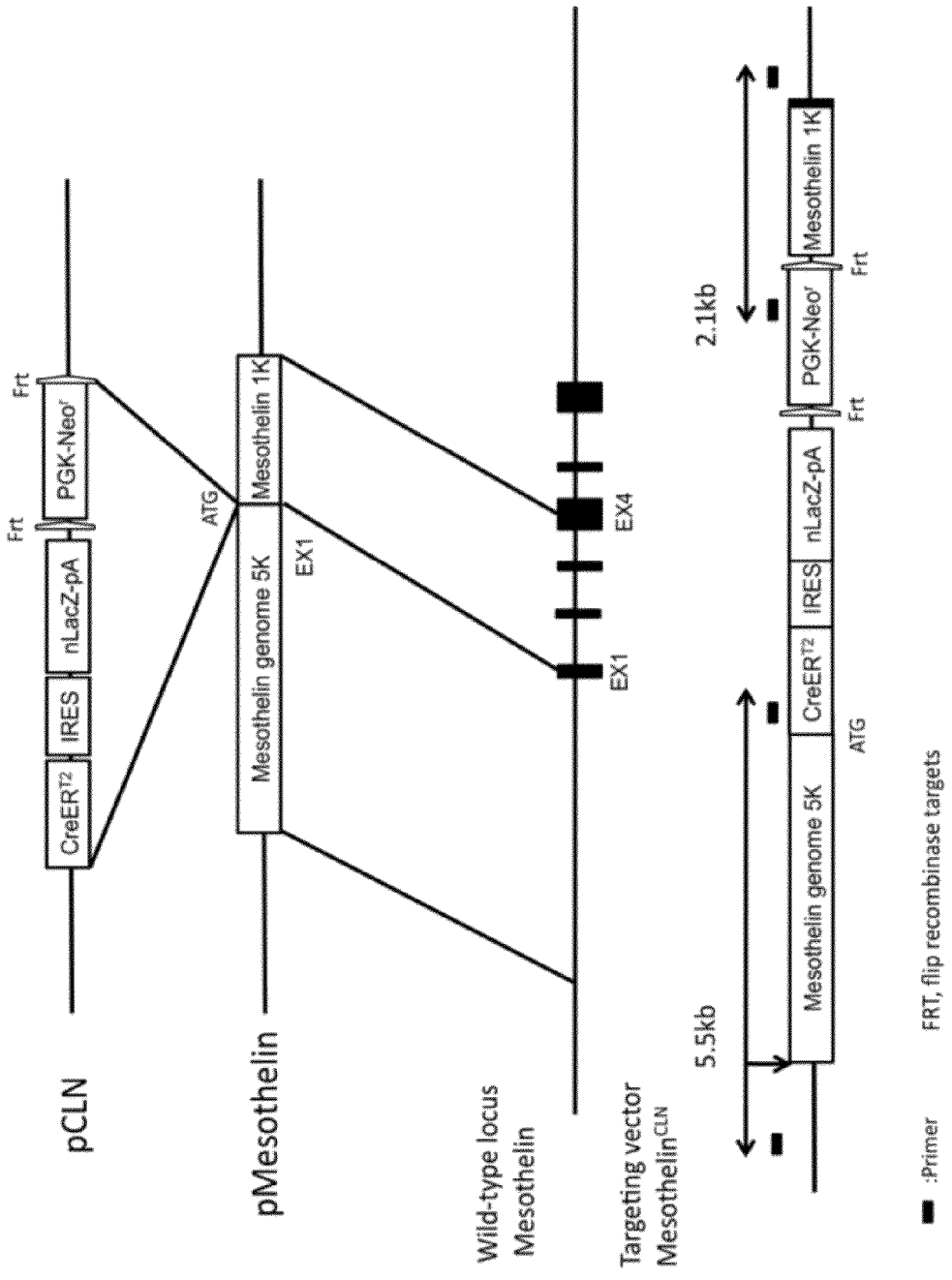
FIG. 4. Genetic lineage tracing of fibroblasts within internal organs. (a) Scheme illustrating the transgenic strategy. The CreER$_{T2}$IRES-lacZ-PGK-neo cassette (pCLN) was introduced into a cassette harboring 6.3-kilobase of the mouse Mesothelin gene (pMesothelin). The Mesothelin-Cre-ER$_{T2}$-IRES-lacZ construct was subsequently transfected into mouse embryonic stem cells. Selected clones were then injected into C57BL/6 blastocysts following the standard protocol to generate chimeras, and by mating these, MSLN$_{CLN}$ mice. (b-d) s-gal staining on sections from MSLN$_{CLN}$ mice, following 2 days post tamoxifen injection. Staining is present within the mesothelium covering the lungs (b, red arrowheads), thymus (c, red arrowheads), and lower digestive system (d, red arrowheads). (e-j) MSLN$_{CLN}$ mice were injected with tamoxifen at e10.5 and analyzed at e17.5. s-gal staining is present within fibroblasts in the lower digestive system (e, f, red arrowheads), mesentery (g, red arrowheads), thymus (h, red arrowheads), parathyroid gland (i, red arrowheads) and liver (j, red arrowheads). Original magnifications: ·4 (c), ·20 (b, d-j).

We knocked into the mouse Mesothelin gene a cassette harboring the CreERT2, nLacZ and the Neomycin resistance constructs (CLN), and created MSLNCLN transgenic mice (FIG. 4a, see 'Methods' section). To genetically label the mesothelium, MSLNCLN offspring were injected with tamoxifen at postnatal day 1 (P1), sacrificed following 2 days post-injection and the internal organs were processed for histology and analyzed for lacZ expression by immunoassaying for beta-galactosidase (β-gal) protein. β-gal staining immunostained the mesothelium surrounding the internal organs including lungs, thymus and lower digestive system in a pattern of expression similar to that of MSLN protein (FIG. 4, b-d, red arrowheads).

Figure 5:
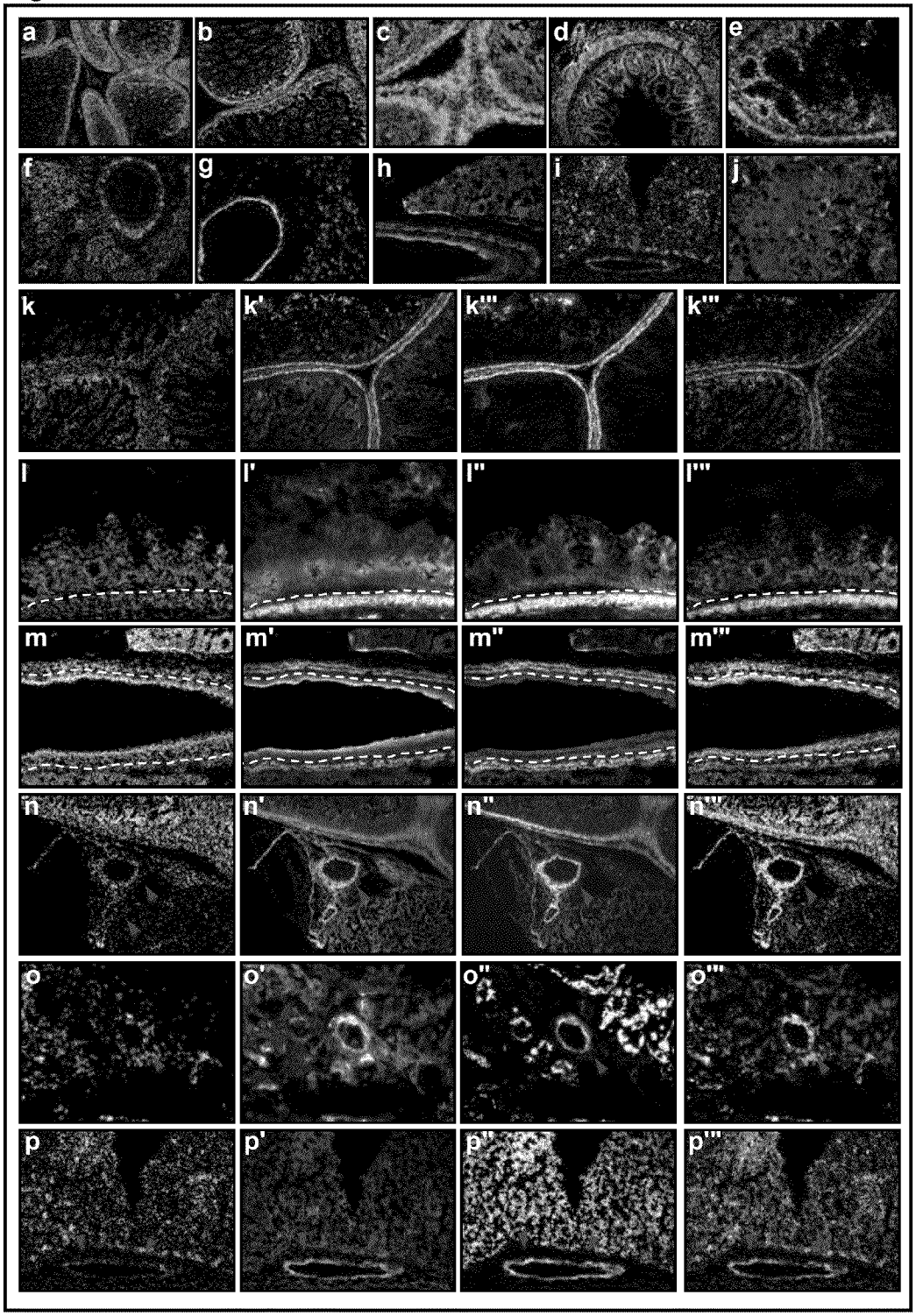
FIG. 5. Genetic lineage tracing of smooth muscle within internal organs, and its vasculature. sgal (a-j, in green) staining is present within the muscular layer of the duodenum (a, b), colon (c) and stomach (d), urinary bladder (e) and ureter (f). s-gal staining within blood vessels of the mesentery (g), lungs (h), liver (i, red arrowhead) and thymus (j, red arrowhead). Note s-gal staining within lung mesothelium (h, red arrowhead). Coexpression of s-gal with α-SMA protein in the duodenum (k-k'''), urinary bladder (l-l'''), pulmonary vasculature (m-m'''), mesentery vasculature (n-n''', red arrowheads), renal vasculature (o-o''', red arrowhead) and liver vasculature (p-p''', red arrowheads). Nuclear DAPI staining (k-p), s-gal staining (k'-p'), α-SMA staining (k''-p''), merged images (k'''-p''', s-gal staining in green, α-SMA staining in red). Dotted lines outline the smooth 17 muscle layer within the urinary bladder (l-l''') and pulmonary vasculature (m-m'''). Original magnifications: ·10 (a-p).

To genetically lineage trace FSMC precursors during embryonic development, MSLNCLN pregnant females where injected with tamoxifen at gestational stage of E10.5 (see materials and methods) and sacrificed at gestational stage of E17.5. Tissues and organs were harvested from the transgenic mice, processed for histology and stained with an antibody against s-gal. Numerous s-gal positive fibroblasts were present within the internal organs including the GI tract's outer serosa and muscular layers, mesentery, thymus and liver (FIG. 4, e-j, red arrowheads). The dermis from cranial, limb and thoracic (dorsal and ventral) regions lacked s-gal positive fibroblasts, in agreement with separate, distinct embryonic origins of fibroblasts for these tissues (23-25). The smooth muscle layer of the lower gastrointestinal system was entirely positive for (β-gal (FIG. 5, a-j). β-gal stained the smooth muscle layers of the stomach, small intestine (duodenum, jejunum, ileum) and large intestine (cecum, colon, rectum), and precisely colocalized with the expression of α-SMA protein, within these layers (FIG. 5, k-k'''). β-gal staining was also present within the submucosal layer of the urinary bladder, where it precisely co-localized with the expression of α-SMA protein (FIG. 5, l-l''').

We looked at other sites in the internal organs that have invested in smooth muscle and connective tissue; mainly the tunica media and adventitia of the vasculature. Within the pleural cavity, β-gal stained the smooth muscle layers of the pulmonary arteries (FIG. 5, h, mm''') and the major blood vessels entering the thymus (FIG. 5j, red arrowhead). β-gal staining within these sites, co-localized precisely with the expression of α-SMA protein. Within the peritoneal cavity, β-gal stained the entire smooth muscle layers of the mesenteric vessels (FIG. 5, n-n''', red arrowheads), renal arteries and blood vessels (FIG. 5, f, o-o''', red arrowheads) and hepatic arteries (FIG. 5, p-p''', red arrowheads), and colocalized precisely with α-SMA protein expression within these vessels.

Figure 6:
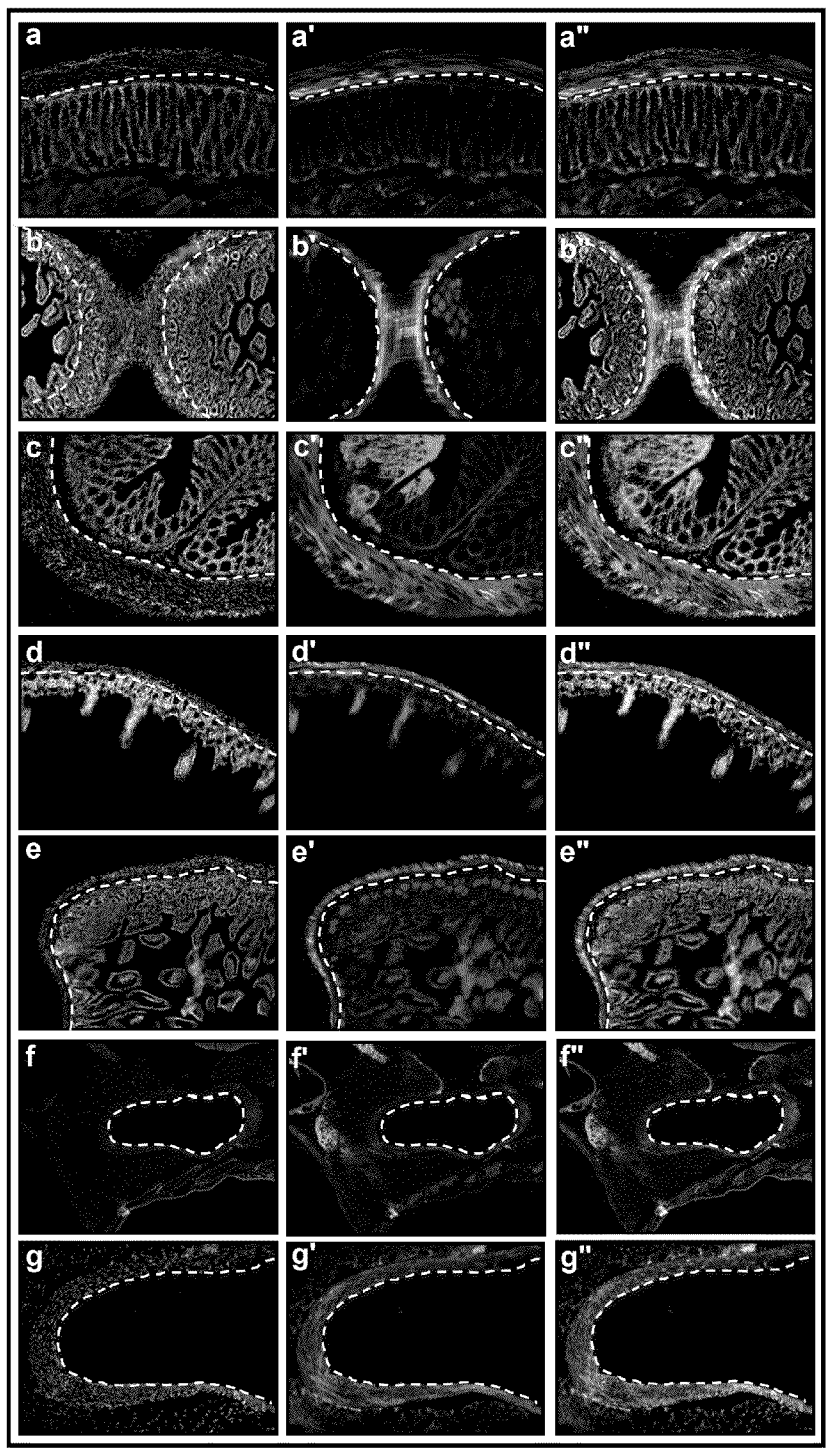
FIG. 6. Polyclonal origins for smooth muscle revealed by clonal analysis of tetrachimeric mice. Sections through jejunum (a-a''), colon (b-b'', c-c''), duodenum (d-d''), cecum (e-e''), cardiovascular (f-f'') and pulmonary artery (g-g''). Nuclear DAPI staining (a-g), tetrachimera image (a'-g'), merged image (a''-g''). Original magnifications: ·4 (f), 0.10 (ae, g). The dotted lines in each figure (a-e) are between the epithelial base of the intestine and the overlying serosal layer, including the mesothelium and the underlying, mainly circumferential smooth muscle. In many places, e.g. in b, one can see the clones extending from mesentery to serosal mesothelium; a subset of the overlying mesothelial clone is continuous with a larger patch of smooth muscle, while other mesothelial cells have different color smooth muscle under them. The epithelial crypts are always a single color, and up to dozens of adjacent crypts are derived from a single intestinal stem cell.

Independently, we analyzed the clonal origins to the smooth muscle layers of the internal organs, and their vasculature by generating tetrachimeric mice, made by injection of mouse embryonic stem cells that stably express separate fluorescent proteins (GFP-mES, RFPmES, CFP-mES) into wild-type blastocysts that were then implanted into pregnant females. Tetrachimeric mice were allowed to reach postnatal stages of development, at which time internal organs, including their vasculature were harvested, sectioned and the derived fluorescent patterns were analyzed. Within the lower digestive system, the smooth muscle layers exhibited a polyclonal pattern, with multiple, separate clones (of the same color) occupying the muscular layer of the stomach, small and large intestines (FIG. 6, a-e). Each of the patchy clones shared, to some extent, the same color with a patch of overlying mesothelium, indicating that the mesothelial lining includes self renewing cells, perhaps stem cells. In the smooth muscle linings of the blood vessels we found a similar polyclonal pattern, with multiple clones occupying the media and adventitia of the blood vessels (FIG. 6, f-g). Thus, multiple FSMCs seed, and contribute cumulatively, to the smooth muscle layers within the internal organs and their vasculature. Whether smooth muscle associates with vessels while they penetrate the organs, or migrate to pre-established vessels is unclear. The mechanisms underlying their migratory patterns will be important to determine.

Figure 9:
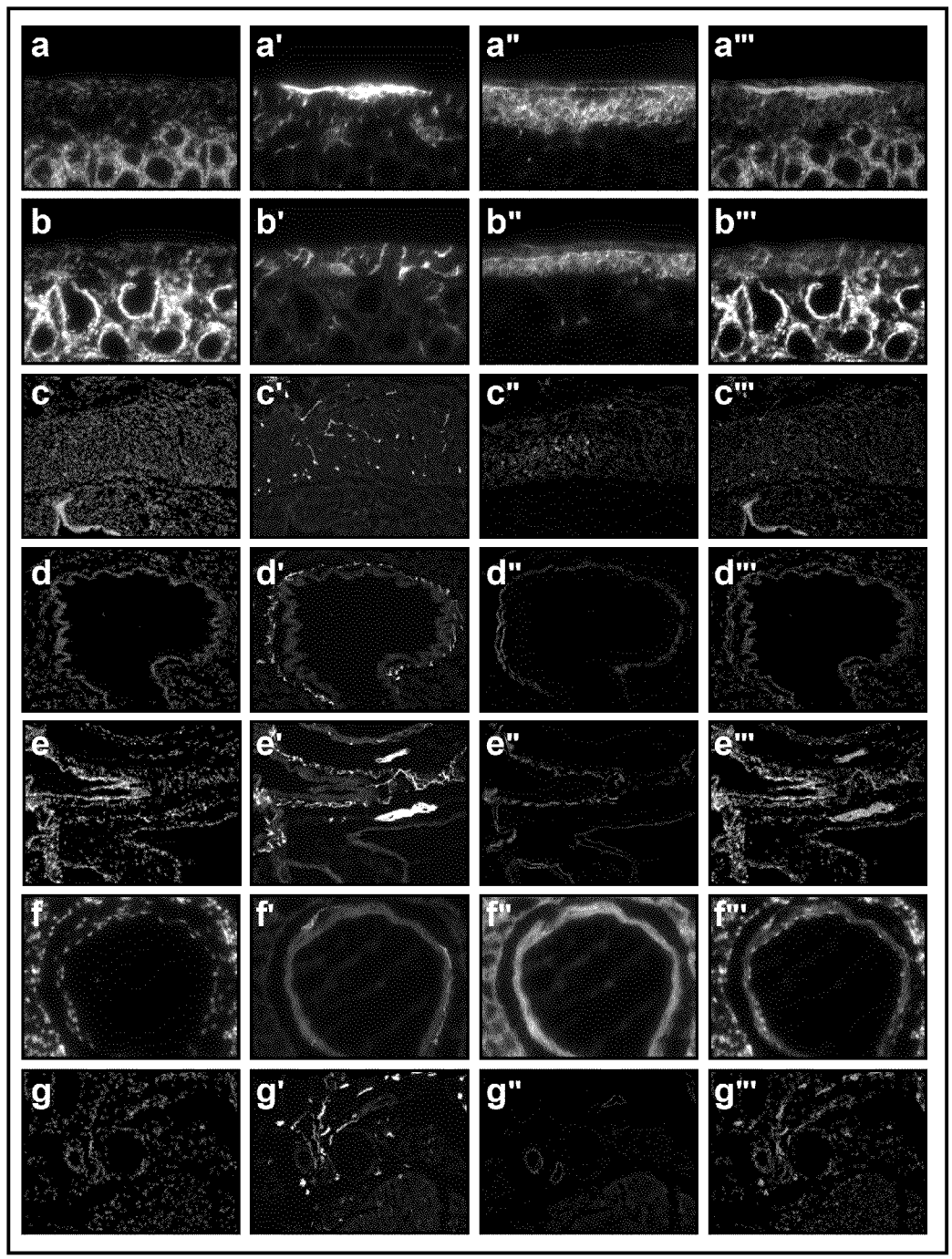
FIG. 9. Minimal contributions to trunk smooth muscle from the neural crest. Sections of Wnt1CremTmG adult mice, through the lower digestive system (a, b), urinary bladder (c), lungs (d), cardiovascular (e), kidney (f) and mesentery (g). Nuclear DAPI staining (a-f), mG expression (a'-f'), α-SMA expression (a"-f"), merged images [mG in green, α-SMA in red](a'''-f'''). Original magnifications: ×20 (a-f).

Negligible Contributions to Trunk FSMCs from Embryonic Neural Crest or Circulating Cells. We then analyzed the contribution of the embryonic neural crest to give rise to smooth muscle within the trunk. We genetically lineage traced the embryonic neural crest using the Wnt1Cre transgenic mouse, which permanently labels early migratory neural crest populations at all axial levels excluding the forebrain. Wnt1Cre transgenic mice were crossed with mTmG, a double-fluorescent reporter mouse that replaces the expression of tomato red with green fluorescent protein (GFP) after Cre-mediated excision. Wnt1Cre$_{mTmG}$ mice were allowed to develop to postnatal stage, at which time internal organs, including their vasculature were harvested, sectioned and the localizations of GFP+ cells were analyzed. Within the digestive and urogenital systems, we found numerous GFP+ cells within the outer serosa and inner muscular layers (FIG. 9, a-c). However, GFP+ cells did not exhibit the layer-specific ubiquitous pattern of seeding of FSMCs (as observed by β-gal staining), nor did they exhibit any similarity to the clonal patterns of smooth muscle as observed in adult tetrachimeric mice, and were mutually exclusive from α-SMA protein expression within these sites (FIG. 9, a'''-c'''). Instead, GFP+ cells displayed long thin cellular processes that penetrated the layers within numerous sites, and that morphologically resembled peripheral nerves.

Along the muscular layer of the digestive system, we found numerous sites where GFP neural plexuses reside and extend processes throughout the smooth muscle layers. Within the vasculature of the internal organs and the mesenteric vessels, GFP+ cells remained within peripheral/circumferential sites and displayed long processes of peripheral nerves but did not appreciably contribute to smooth muscle layers of blood vessels, and were mutually exclusive from α-SMA protein expression within these sites (FIG. 9, d-g). These results are consistent with findings of neural crest derived cardiovascular malformations with normal smooth muscle differentiation, and together imply that congenital abnormalities and postnatal vascular pathologies previously associated with neural crest, arise from malfunction/maldevelopment of peripheral nerves innervating these tissues and not from a direct cellular contribution to smooth muscle.

Figure 10:
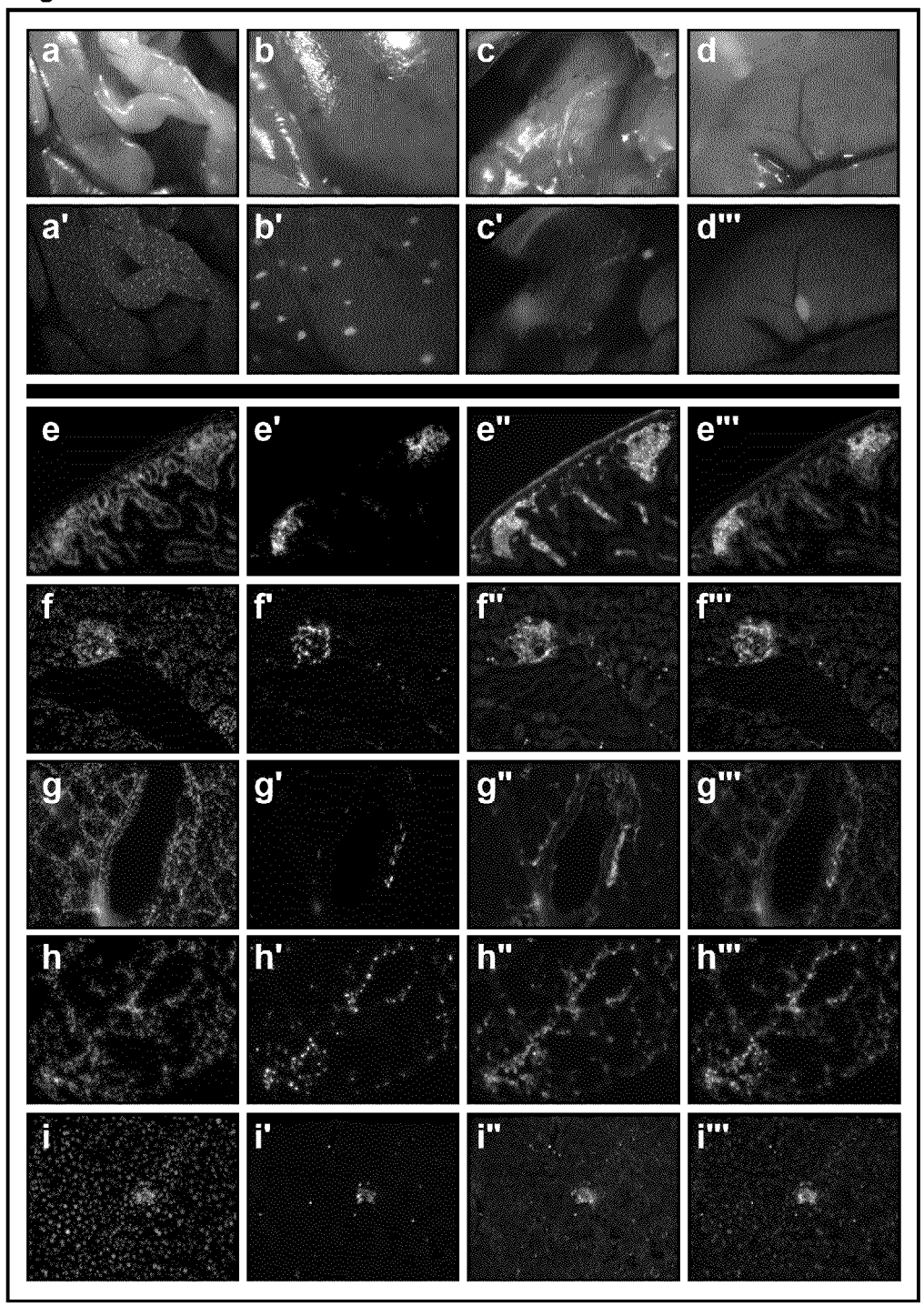
FIG. 10. Minimal contributions of circulating cells to trunk smooth muscle. Images of the mouse abdominal cavity following 1 year of parabiosis. Images of small intestine (a), large intestine (b), mesentery (c) and lymph nodes (d). Sections of representative organs from parabiosed mice (e-i). Duodenum (e), kidney (f), urinary bladder (g), lung (h) and liver (i). Fluorescent images (a-d), bright-field images (a'-d'). Nuclear DAPI staining (e-i), GFP expression (e'-i'), CD45 expression (e"-i"), merged images (e'''-i'''). Original magnifications: ·9 (a-c), ×20 (e-i), ·31 (b, d).

We then tested whether any circulating cells could contribute to FSMCs of the internal organs, and their vasculature, by creating pairs of genetically marked parabiotic mice that have a shared anastomosed blood circulatory system. Wild-type mice were surgically conjoined to mice expressing GFP under the chicken β-actin promoter. Mice were left parabiosed for 1 year following which, chimerism was assayed within the hematopoietic system, at which time parabiosed wild-type mice were sacrificed and the internal organs, including their vasculature, were analyzed for the presence of donor-derived GFP+ cells. Donor derived GFP+ cells were present within numerous sites within internal organs, including lungs, liver, the lower digestive system, in Peyer's patches and mesenteric lymph nodes (FIG. 10, a-d). Tissues and organs were harvested, processed for histology and immunoassayed for the pan-hematopoietic marker CD45. GFP+ cells and cell foci within these organs co-expressed the hematopoietic antigen CD45 within all sites examined, and failed to show any contribution to the respective organ's mesothelium or to FSMCs, including the vasculature (FIG. 10, e-i), in agreement with a previous publication that shows minimal contributions of transplanted hematopoietic stem cells, to non hematopoietic tissues.

Our analysis of the mesothelium shows a developmental restriction to smooth muscle and fibroblasts throughout the internal organs. We find no contribution to heart muscle. Genetic lineage tracing reveals that MSLN expressing precursors, and not neural crest or circulating cells, represent the major, if not the only contributors to smooth muscle of the trunk. These results also establish MSLN as a novel marker of FSMC precursors. The identification and prospective isolation of FSMC precursors represents a major advancement towards their targeting for regenerative medicine purposes, including the clinical investigation into the etiology and progression of their respective tumors.

Methods

Mice. Mice were bred and maintained at the Stanford University Research Animal Facility in accordance with Stanford University guidelines. All the animals were housed in sterile micro-insulators and given water and rodent chow ad libitum.

Histology and Tissue Analysis For fixation, tissues and organs were placed in 2% paraformaldehyde for 12-16 h at 4° C. Samples were prepared for embedding by soaking in 30% sucrose in PBS at 4° C. for 24 h. Samples were removed from the sucrose solution and tissue blocks were prepared by embedding in Tissue Tek O. C. T (Sakura Finetek) under dry ice to freeze the samples within the compound. Frozen blocks were mounted on a MicroM HM550 cryostat (MICROM International GmbH) and 5-8 micron thick sections were transferred to Superfrost/Plus adhesive slides (Fisher brand).

Immunohistochemistry Immunostaining was performed using the following primary antibodies PECAM-1/CD31 (Abcam), MECA-32 (Biolegend), FSP1 (Abcam), Vimentin (Abcam), α-SMA (Abcam), Mesothelin (Abbiotec), CD45 (Biolegend), Type IV Collagen (Abcam), Type I Collagen (Abcam), Fibronectin (Abcam). Briefly, slides were fixed in cold acetone (−20° C.), and then blocked for 30 min in 10% BSA with 2% goat serum followed by incubation with primary antibody for 12-16 hours. Alexa Fluor 594 conjugate anti-rabbit or anti-rat antibodies (Invitrogen) were used as secondary and incubated for 1 hour. Fluorescent and bright-field images were taken with a Leica DM4000B microscope (Leica Microsystems) and RETIGA 2000R camera (QImaging Scientific Cameras).

Transplantation and Culturing of Adult Mesothelium. Mesothelial tissues were harvested from Actin-eGFP adult mice underneath a stereomicroscope, using a micro dissecting scissor and tweezers (Roboz). Tissues were washed several times in phosphate buffered saline (PBS) and placed in PBS on ice until transplantation or culturing. Male and female adult Rag(−/−) gamma chain(−/−) mice were anesthetized with Isoflurane (2-chloro-2-(difluoromethoxy)-1,1,1-trifluoro-ethane) and placed underneath a stereomicroscope. The ventral skin was shaved to remove residual hair. Betadine antiseptic was applied topically to the skin and an incision was made along the ventral skin and peritoneal wall to expose the abdominal cavity. Small tissues of mesothelium were placed within the host cavity, underneath the mesothelium covering the stomach, jejunum, mesentery or peritoneal wall. The peritoneal wall was then sutured with a 5-0 nylon suture (Ethicon) and the skin was closed using an autoclip applier (Stoelting). Mice were then placed in sterile micro-insulators, separately, with antibiotics, initially for two weeks.

FACS Sorting of Mesothelial Cells Mesothelial tissues were harvested from the internal organs and placed in a dissociation buffer containing collagenase (1 mg/ml) and DNAse (10 u/ml) for 15-30 minutes at 37° C. then filtered through a 100 micron filter and placed in a staining media containing 2% FCS in PBS. The following antibodies were used:

Time Lapse Video of Adult Mesothelium Mesothelium tissues were grown in a chambered coverglass system (Lab-Tek II, Nunc). Live cell imaging was performed on a Zeiss 200M inverted microscope encased in a perspex chamber that was heated to 37° C. Plates were placed in a smaller internal chamber that was continuously perfused with humidified 5% $CO_2$. The set up included a motorized stage that enabled simultaneous imaging of multiple fields. Digital (12-bit) images were acquired with a cooled CCD camera (Photometrics CoolSNAP HQ) and phase contrast with a ·20 n.a. 0.8 air objective. The entire set-up was controlled by Metamorph software and ImageJ was used for image processing, analysis and assembly.

Generation of $MSLN^{cre}ER^{T2}$ mice. The 6.3-kilobase (kb) of the mouse Mesothelin gene (Long arm/5.1 kb upstream of the ATG start codon and Short arm/1.2 kb downstream of ATG) was cloned from the 129×1/svj strain genomic DNA (The Jackson Laboratory). The ATG start codon was then replaced by the $CreER_{T2}$IRES-lacZ-PGK-neo cassette. Neomycin-resistant recombinant ES clones were selected in medium containing G418 and were picked into two 96-well plates and cultured to 70% confluence. Plates were then duplicated, one cryo-preserved and one that continued culture to 100% confluence for DNA isolation. DNA from all clones was screened for the correct targeting by long PCR (Platinum Taq polymerase high fidelity, Invitrogen) with primers flanking the Long and Short homology arm sites to inserted cassette sites. All positive clones were confirmed by another long PCR. Positive clones were thawed, expanded and injected into C57BL/6 blastocysts following the standard protocol. Chimaeras were mated with C57BL/6 mice and the germline transmission in agouti offspring were confirmed by PCR genotyping. The neomycin selection cassette was later excised in vivo by crossing with Rosa26-FLPe mice (The Jackson Laboratory).

What is claimed is:

1. A method of enrichment for a composition of FSMC progenitor cells, wherein at least 80% of the cells in said composition are characterized as mesothelin (MSLN)$^+$ and lineage panel (lin)$^−$; the method comprising:
   dissociating mesothelium to provide a population of dissociated cells;
   combining reagents that specifically recognize mesothelin, one or more lineage panel markers selected from Tie2, CD31, CD45 and Ter119, and one or more surface markers selected from Thy1 (CD90) and CD34 with said sample of cells; and
   selecting for those cells that are MSLN$^+$, lin$^−$ and one or more of Thy1$^{high}$ and CD34$^{high}$, wherein the lineage panel comprises one or more markers selected from Tie2, CD31, CD45 and Ter119;
   said composition being enriched for cells that are FSMC progenitors capable of giving rise to both fibroblasts and smooth muscle cells, said FSMC progenitors having a surface phenotype of Thy1$^{high}$, CD34$^{high}$, CD44$^{low}$ and CD105$^{low}$.

2. The method of claim 1, wherein the cells are mouse cells.

3. The method of claim 1, wherein the cells are human cells.

4. The method of claim 1, wherein the selecting comprises selecting for cells having a surface phenotype comprising Thy1$^{high}$.

5. The method of claim 1, wherein the selecting comprises selecting for cells having a surface phenotype comprising CD34$^{high}$.

6. The method of claim 1, wherein the mesothelium is adult mesothelium.

7. The method of claim 1, wherein the method further comprises differentiating said FSMC progenitors into fibroblasts.

8. The method of claim 1, wherein the method further comprises differentiating said FSMC progenitors into smooth muscle cells.

9. A method of enrichment for a composition of FSMC progenitor cells, wherein at least 80% of the cells in said composition are characterized as mesothelin (MSLN)$^+$ and lineage panel (lin)$^−$; the method comprising:
   dissociating mesothelium to provide a population of dissociated cells;
   combining reagents that specifically recognize mesothelin, the lineage panel markers Tie2, CD31, CD45, and Ter119, and one or more of Thy1 (CD90) and CD34 with said sample of cells; and
   selecting for those cells that are MSLN$^+$ lineage panel negative, wherein the lineage panel comprises Tie2, CD31, CD45, and Ter119, and one or more of Thy1$^{high}$ and CD34$^{high}$;
   said composition being enriched for cells that are FSMC progenitors capable of giving rise to both fibroblasts and smooth muscle cells, said FSMC progenitors having a surface phenotype of Thy1$^{high}$, CD34$^{high}$, CD44$^{low}$ and CD105$^{low}$.

* * * * *